United States Patent [19]

Lile et al.

[11] Patent Number: 5,606,031
[45] Date of Patent: Feb. 25, 1997

[54] PRODUCTION AND PURIFICATION OF BIOLOGICALLY ACTIVE RECOMBINANT NEUROTROPHIC PROTEIN IN BACTERIA

[76] Inventors: Jack Lile, 947 Casitas Vista Rd., Ventura, Calif. 93001; Tadahiko Kohno, 1557 Hays Ct., Louisville, Colo. 80027; Duane Bonam, 4 Morsecroft La., Amesbury, Mass. 01913; Mary S. Rosendahl, 310 Fairplay, Broomsfield, Colo. 80020

[21] Appl. No.: 266,080

[22] Filed: Jun. 27, 1994

Related U.S. Application Data

[63] Continuation-in-part of Ser. No. 240,122, May 9, 1994, abandoned, which is a continuation-in-part of Ser. No. 87,912, Jul. 6, 1993, abandoned, which is a continuation of Ser. No. 680,681, Apr. 4, 1991, abandoned, which is a continuation-in-part of Ser. No. 594,126, Oct. 9, 1990, Pat. No. 5,235,043, Ser. No. 547,750, Jul. 2, 1990, abandoned, and Ser. No. 505,441, Apr. 6, 1990, abandoned.

[51] Int. Cl.$^6$ .............................. C07K 1/18; C07K 1/36; C12N 15/12
[52] U.S. Cl. ...................... 530/416; 530/402; 530/408; 530/417
[58] Field of Search ................ 435/252.3, 252.33, 435/320.1; 530/350, 404, 405, 416, 417, 402, 408; 536/23.1, 23.5

[56] References Cited

U.S. PATENT DOCUMENTS

| | | | |
|---|---|---|---|
| 4,223,967 | 9/1980 | Bobbit et al. | 530/351 |
| 4,421,685 | 12/1983 | Chance et al. | 530/303 |
| 4,451,396 | 5/1984 | DiMarchi | 530/402 |
| 4,511,502 | 4/1985 | Builder et al. | 530/417 |
| 4,511,503 | 4/1985 | Olson et al. | 530/422 |
| 4,512,922 | 4/1985 | Jones et al. | 530/408 |
| 4,518,526 | 5/1985 | Olson | 530/351 |
| 4,599,197 | 7/1986 | Wetzel | 530/405 |
| 4,620,948 | 11/1986 | Builder et al. | 530/419 |
| 5,169,762 | 12/1992 | Gray et al. | 435/69.1 |
| 5,169,764 | 12/1992 | Shooter et al. | 435/69.7 |
| 5,180,820 | 1/1993 | Barde et al. | 536/23.51 |
| 5,235,043 | 8/1993 | Collins et al. | 530/399 |

FOREIGN PATENT DOCUMENTS

| | | |
|---|---|---|
| 1220736 | 4/1987 | Canada . |
| 0121338 | 10/1984 | European Pat. Off. . |
| 0361830 | 9/1989 | European Pat. Off. . |
| 0336324 | 10/1989 | European Pat. Off. . |
| WO91/03569 | 3/1991 | WIPO . |

OTHER PUBLICATIONS

Cleland et al., "Cosolvent Assisted Protein Refolding," Biotechnology, vol. 8, Dec. 1990, pp. 1274–1278.
Cleland et al. (1992) Jour. of Biological Chemistry 267:13327–13334.
Cleland et al. (1990) Biotechnology 8:1274.
Gonzales et al. (1990) J. Agric. Food Chem. 38:149–153.
Leibrock et al. (1989) Nature 341:149.
Light et al. (1985) Bio Techniques 3:298–305.
Spalding (1991) Bio/Technology 9:229.
Dicou et al. (1989) J. Neurosci. Res. 22:13.
Edwards et al. (1986) Nature 319:784.
Edwards et al. (1988) Molec. Cell. Biol. 8:2456.
Iwai et al. (1986) Chem. Parm Bull. 34:4724.
Kohno (1990) Methods Enzymol. 185:187.

*Primary Examiner*—Marianne P. Allen
*Attorney, Agent, or Firm*—Swanson & Bratschun LLC

[57] ABSTRACT

A process for the production of biologically active recombinant neurotrophic factor from the NGF/BDNF family is described. The process is comprised of a) constructing a synthetic neurotrophic factor gene suitable for expression in a bacterial expression system; b) the synthetic neurotrophic factor gene is expressed in a bacterial expression system; c) the neurotrophic factor is solubilized and sulfonylated; d) sulfonylated neurotrophic factor is allowed to refold in the presence of polyethylene glycol and urea; and e) biologically active neurotrophic factor is isolated and purified.

22 Claims, 12 Drawing Sheets

```
bdnf  ATG  CATCCTTTTCCTTACTATGGTTATTTCATACTTTGGTTGCATGAAGGCTGCCCCCATGAAAGA
ngf        ATGTCCATGTTGTTCTACACTCTGATCACAGCTTTTCTGATCGGCATACAGGCGAACCACACTCAGA AGCAAACATCCGAGGACAAGGT------GGCTTGGCCTACCCAGGTGTGCGG---ACC------CATGGGACTCT
GAGCAATGTCCCTGCA---GGA---CAC------ACCATCCCCAAGTCCACTGGACTAAACTTCAGCATTCCCT GGAGAGC------GTGAATGGGCCCAAGGCAGGTTCAAGAGGCTTGACATCATTGGCTGACACTTTCGAACACGT
TGAC------ACTGCC----CTTCGCAGAGCC---CGCAGCGCC---CCG---GCAGCGGCGATAGCTGCACGCGT GATAGAAGAGCTGTTGGATGAGGAC---CAGAAAGTTCGGCCCAATGAAGAAAC------AATAAGGACGAGA
GGCGGGG---CAGACCCGC---AACATT---ACTGTG------GACCCCAGGCTGTTT---AAAAAGCGGCG CTTGTACACGTCCAGGGTGATGCTCAGTAGTCAAGTGCCTTTGGAGCCCTCTTCTCTTCTCTTTCTGCTGGAGAATA
ACTCCGTTCACCCGTTGCTGTTTAGCACCCAGCCTCCCGTGAAGCTGCAGACACTCAGGATCTGGACTTCGA CAAAAATTACCTAGATGCTGCAAACATGTCCATGAGGGTCCGGC------CACTCTGACCCTGCCCGCCGAGG
GGTCGGTGGTGCTGCCCCCTTCAACAGGACTCACAGGAGCAAGCGGTCATCATCCCATCTTCCACAGGGG GGAGCTGAGCCGTGTGTGAGCAGTATTAGTGAGTGGGTAACGGCGGCACAAAAAGACTGCAGTGGACATGTCGG
CGAATTCTCGGTGTGTGAGCAGTGTCAGCGTGTGGGTTGGG------GATAAGACCACCGCCACAGACATCAAGGG CGGGACGGTCACAGTCCCTGAAAAGGTCCCTGTATCAAAAGGCCAACTGAAGCAATACTTCTACGAGACCAAGTG
CAAGGAGGTGATGGTGTTGGGAGAGGTGAACATTAACAACAGTGTATTCAAACAGTACTTTTTGAGACCAAGTG CAATCCCATGGGTTACACACAAAGGAGGCTGCAGGGGCATAGACAAAAGGCATTGGAACTCCCAGTGCCGAACTAC
CCGGGACCCCAAATCCCGTTGACAGCGGGTGCCGGGGCATTGACTGACACTGAACTCATATTGTACCACGAC CCAGTCGTACGTGCGGGCCCTTACCATGGATAGCAGAAAGAGAATTGGCTGGCGATTCATAAGGATAGACACTTC        bdnf  (SEQ ID NO:1)
TCACACCTTTGTCAAGGCGCTGACCATGGATGGC---AAGCAGGCTGCCTGCGGTTTATCCGGATAGATACGGC      ngf   (SEQ ID NO:2)

TTGTGTATGTACATTGACCATTAAAAGGGGAAGATAG
CTGTGTGTGTGTGCTCAGCAGGAAGGCTGTGAGAGAGCCTGA
```

FIG. 1

| bdnf | Met | Thr | Ile | Leu | Phe | Leu | Thr | Met | Val | Ile | Ser | Tyr | Phe | Gly | Cys | Met | Lys |
|---|---|---|---|---|---|---|---|---|---|---|---|---|---|---|---|---|---|
| ngf | Met | Ser | Met | Leu | Phe | Tyr | Thr | Leu | Ile | Thr | Ala | Phe | Leu | Ile | Gly | Ile | Gln |
| Ala | Pro | Met | Lys | Glu | Ala | Asn | Ile | Arg | Gly | Gln | Gly | — | — | Gly | Leu | Ala | Tyr |
| Ala | Glu | Pro | His | Ser | Asn | Asn | Val | Pro | Ala | — | — | His | — | — | — | Thr | Ile |
| Pro | Gly | Val | Arg | — | — | — | — | His | Gly | Leu | Glu | Ser | — | — | — | Val | Asn | Gly |
| Pro | Gln | Val | His | Trp | Thr | Lys | Leu | Gln | His | Ser | Leu | Asp | — | — | — | Thr | Ala | — | — | Leu |
| Pro | Lys | Ala | Gly | Ser | Arg | Gly | Leu | Thr | Ser | Leu | Ala | Asp | Thr | Phe | Glu | His | Val | Ile |
| Arg | Arg | Ala | — | — | Arg | Ser | Ala | Pro | — | — | — | Ala | Ala | Ile | Ala | Arg | Val | Ala |
| Glu | Glu | Leu | Leu | Asp | Glu | Gln | — | — | Gln | Lys | Val | Arg | Pro | Asn | Gln | Glu | — | — | — | — |
| Gly | — | — | Gln | Thr | Arg | Asn | Ile | — | — | Thr | Val | — | — | Asp | Pro | Arg | Leu | Phe |
| Asn | Lys | Asp | Ala | Asp | Leu | Tyr | Thr | Ser | Arg | Val | Met | Leu | Ser | Ser | Gln | Val | Pro | Leu |
| — | — | Lys | Lys | Arg | Leu | Ser | Pro | Arg | Val | Leu | Phe | Ser | Thr | Gln | Pro | Pro | Arg |
| Glu | Pro | Leu | Phe | Leu | Gln | Glu | Glu | Asp | Phe | Tyr | Asn | Leu | Asp | Ala | Ala | Ala | Asn |
| Glu | Ala | Asp | Thr | Gln | Asp | Leu | Lys | Val | Gly | Glu | Phe | Gly | Tyr | Ala | Pro | Phe | Asn |
| Met | Ser | Arg | Val | Arg | Arg | — | — | His | Ser | Ala | Pro | Arg | Gly | Arg | Gly | Glu | Leu |
| Arg | Thr | His | Arg | Lys | Arg | Ser | Ser | His | Pro | Ile | Phe | His | Arg | Gly | Glu | Phe |
| Ser | Val | Cys | Asp | Ser | Ile | Ser | Glu | Trp | Val | Thr | Ala | Ala | Asp | Lys | Lys | Thr | Ala | Val |
| Ser | Val | Cys | Asp | Ser | Val | Ser | Val | Trp | Val | Gly | — | — | Asp | Lys | Thr | Ala | Thr |
| Asp | Met | Ser | Gly | Gly | Thr | Val | Thr | Val | Leu | Glu | Lys | Val | Pro | Val | Ser | Lys | Gly | Gln |
| Asp | Ile | Lys | Gly | Lys | Glu | Val | Met | Val | Leu | Gly | Glu | Val | Asn | Ile | Asn | Asn | Ser | Val |
| Leu | Lys | Gln | Tyr | Phe | Tyr | Glu | Thr | Lys | Cys | Asn | Pro | Met | Gly | Tyr | Thr | Lys | Glu | Gly |
| Phe | Lys | Gln | Tyr | Phe | Phe | Glu | Thr | Lys | Cys | Arg | Asp | Pro | Asn | Pro | Val | Asp | Ser | Gly |
| Cys | Arg | Gly | Ile | Asp | Lys | Arg | His | Trp | Asn | Ser | Gln | Cys | Arg | Thr | Thr | Gln | Ser | Tyr |
| Cys | Arg | Gly | Ile | Asp | Ser | Lys | His | Trp | Asn | Ser | Tyr | Cys | Thr | Thr | Thr | His | Thr | Phe |
| Val | Arg | Ala | Leu | Thr | Met | Asp | Ser | Arg | Lys | Arg | Ile | Gly | Trp | Arg | Phe | Ile | Arg | Ile |
| Val | Lys | Ala | Leu | Thr | Met | Asp | Gly | Lys | — | — | Gln | Ala | Ala | Trp | Arg | Phe | Ile | Arg |
| Asp | Thr | Ser | Cys | Val | Cys | Thr | Leu | Thr | Ile | Lys | Arg | Gly | Arg | (SEQ ID NO:3) |
| Asp | Thr | Ala | Cys | Val | Cys | Val | Leu | Ser | Arg | Lys | Ala | Val | Arg | Arg | Ala | (SEQ ID NO:4) |

```
BamHI                                              EcoRI
GGATCCAATAAGGAGGAAAAAAATGTCTAGCAGCCACCCGATCTTTCATCGTGGCGAATTCTCTGTATG
CCTAGGTTATTCCTCCTTTTTTTACAGATCGTCGGTGGGCTAGAAAGTAGCACCGCTTAAGAGACATAC
                        Met Ser Ser Ser His Pro Ile Phe His Arg Gly Glu Phe Ser Val Cys
                                                                                      70

CGATTCCGTTAGCGTTTGGGTTGGGCGACAAAACCACTGCTACTGACATCAAAGGTAAAGAAGTAATGGTT
GCTAAGGCAATCGCAAACCCAACCGCTGTTTTGGTGACGATGACTGTAGTTTCCATTTCTTCATTACCAA
Asp Ser Val Ser Val Trp Val Gly Asp Lys Thr Thr Asp Ile Lys Gly Lys Glu Val Met Val
                                                                                     140

CTGGGGCGAAGTTAACATCAACAATTCTGTTTTTAAACAGTACTTCTTCGAAACCAAATGCCGCGACCCGA
GACCCGCTTCAATTGTAGTTGTTAAGACAAAATTTGTCATGAAGAAGCTTTGGTTTACGGCGCTGGGCT
Leu Gly Glu Val Asn Ile Asn Asn Ser Val Phe Lys Gln Tyr Phe Phe Glu Thr Lys Cys Arg Asp Pro
                                                                                     210
```

```
SalI
ACCCGGTCGACTCCGGCTGCCGGTGGTATCGACTCTAAACACTGGAACTCCTACTGCACCACTACTCACAC
     +----+----+----+----+----+----+----+----+----+----+----+----+----+----  280
TGGGCCAGCTGAGGCCGACGGCCACCATAGCTGAGATTTGTGACCTTGAGGATGACGTGGTGATGAGTGTG
Asn Pro Val Asp Ser Gly Cys Arg Gly Ile Asp Ser Lys His Trp Asn Ser Tyr Cys Thr Thr Thr His Thr

CTTCGTTAAAGCTCTGACCATGGACGGCAAACAGGCTGCATGGCCGTTTATTCGTATTGACACCGCATGT
     +----+----+----+----+----+----+----+----+----+----+----+----+----+----  350
GAAGCAATTTCGAGACTGGTACCTGCCGTTTGTCCGACGTACCGGCAAATAAGCATAACTGTGGCGTACA
Phe Val Lys Ala Leu Thr Met Asp Gly Lys Gln Ala Ala Trp Arg Phe Ile Arg Ile Asp Thr Ala Cys

KpnI
GTTTGCGTACTGAGCCGCAAAGCTGTTCGTTAAGGTACC
     +----+----+----+----+-- 389
CAAACGCATGACTCGGCCGTTTCGACAAGCAATTCCATGG
Val Cys Val Leu Ser Arg Lys Ala Val Arg •        (SEQ ID NO:5)
```

FIG. 3B

NGF Mut 1
5'-CGA TTC CGT TAG C[GT TTG GGT T]GG CGA CAA AA-3'  32
(SEQ ID NO:6)
Tm=96°C

NGF Mut 2
5'-CTT CTT CGA A[A]C CAA ATG CCG-3'  21
(SEQ ID NO:7)
Tm=62°C

NGF Mut 3
5'-CAC TGG AAC T[CC] TAC TGC ACC A-3'  22
(SEQ ID NO:8)
Tm 48+20=68°C

FIG. 4

Syn NGF 5P

1. TP NGF

5'-GGA TCC AAG AAG GAG ATA TAC ATA TG TCT AGC AGC -3'    35
(SEQ ID NO:9)

FIG. 5

2. REP NGF

5'-TGC CAA GCT TGG ATC CAA GAA GGA GAT ATA CAT ATG TCA TCA T-3'    43
(SEQ ID NO:10)

5'-GGC TGT GAG ATA AGG TAC CGA CAT TGC CTG ATG GCG CTG TGC GTG TCA GGC CTA CGG GGA GCA TCG
TAG GCC GGG CAA GGC ACA GCC GCC ATC CGG CGT GCC CAA GCT TGG ATC CCC GG-3'    119
(SEQ ID NO:11)

FIG. 6

BamTP Δ 53 Sequence (EcoRI, BamHI, and HindIII sites highlighted)
(SEQ ID NO:12)

```
GCT GTT GAC AAT TAA TCA TCG GCT CGT ATA ATG TGT GGA ATT GTG AGC GGA TAA
                                                                          BamHI
                            EcoRI

CAA TTT CAC ACA GGA AAC AGA ATT CCA CAA CGG TTT CCC TCT AGA AAT AAT TTT GTT TGG

ATC CAA GAA GGA GAT ATA CAT ATG TTG CCC GCC CAG GTG GCA TTT ACA
                                Met Leu Pro Ala Gln Val Ala Phe Thr

CCC TAC GCT CCG GAA CCG GGT TCT ACC TGC GAA CTC CGG AGA TAC TAT GAC CAG
Pro Tyr Ala Pro Glu Pro Gly Ser Thr Cys Glu Leu Arg Arg Tyr Tyr Asp Gln

ACA GCT CAG ATG TGC AGC AAG TGC TCG CCG GGC CAA CAT GCA AAA GTC TTC
Thr Ala Gln Met Cys Ser Lys Cys Ser Pro Gly Gln His Ala Lys Val Phe

TGT ACC AAG ACC TCG GAC ACC GTG TGT GAC TCC GAG TGT AGC ACA TAC ACC
Cys Thr Lys Thr Ser Asp Thr Val Cys Asp Ser Glu Cys Ser Thr Tyr Thr

CAG CTC TGG AAC TGG GTT CCC GAG TGC TTG AGC TGT GGC TCC CGC TGT AGC TCT
Gln Leu Trp Asn Trp Val Pro Glu Cys Leu Ser Cys Gly Ser Arg Cys Ser Ser

GAC CAG GTG GAA ACT CAA GCC TGC ACT CGG GAA AAG CAG GAG AAC CGC ATC TGC ACC TGC
Asp Gln Val Glu Thr Gln Ala Cys Thr Arg Glu Lys Gln Glu Asn Arg Ile Cys Thr Cys

AGG CCC GGC TAC TGC TAC TGC GCG CTG AGC CTG AAG CAG GGG TGC CGG CTG TGC GCG
Arg Pro Gly Tyr Cys Tyr Cys Ala Leu Ser Leu Lys Gln Gly Cys Arg Leu Cys Ala

CCG CTG CGC AAG TGC CGC GGC TTC GGC GTG GCC AGA CCA GGA ACT GAA ACA
Pro Leu Arg Lys Cys Arg Gly Phe Gly Val Ala Arg Pro Gly Thr Glu Thr
```

FIG. 7A

```
TCA GAC GTG GTG TGC AAG CCC TGT GCC CCG GGG ACG TTC TCC AAC ACG ACT TCA
Ser Asp Val Val Cys Lys Pro Cys Ala Pro Gly Thr Phe Ser Asn Thr Thr Ser

TCC ACG GAT ATT TGC AGG CCC CAC CAG ATC TGT AAC GTG GTG GCC ATC CCT GGG
Ser Thr Asp Ile Cys Arg Pro His Gln Ile Cys Asn Val Val Ala Ile Pro Gly

HindIII
                                                      ------
AAT GCA AGC AGG GAT GCA GTC TGC ACG TCC ACG TCC TAA GCTT
Asn Ala Ser Arg Asp Ala Val Cys Thr Ser Thr Ser
```

FIG. 7B

2 Start (-)

(SEQ ID NO:13)
```
              *   *         *
5'-TCA AGG GCA AAG AAG TGA TGG TAT TGG GAG AGG-3'        30
```

FIG. 8

PRODUCTION AND PURIFICATION OF BIOLOGICALLY ACTIVE RECOMBINANT NEUROTROPHIC PROTEIN IN BACTERIA

CROSS-REFERENCE TO RELATED APPLICATIONS

This is a continuation-in-part of U.S. application Ser. No. 08/240,122 filed May 9, 1994, now abandoned which is a continuation-in-part of U.S. application Ser. No. 08/087,912 filed Jul. 6, 1993, now abandoned, which is a file wrapper continuation of U.S. application Ser. No. 07/680,681 filed Apr. 4, 1991, now abandoned, and a continuation-in-part of U.S. application Ser. No. 07/594,126 filed Oct. 9, 1990, issued as U.S. Pat. No. 5,235,043, U.S. application Ser. No. 07/547,750 filed Jul. 2, 1990, now abandoned and U.S. application Ser. No. 07/505,441 filed Apr. 6, 1990, now abandoned, each of which is entitled "Production of Biologically Active, Members of the NGF/BDNF Family of Neurotrophic Protein".

FIELD OF THE INVENTION

This invention relates to processes for the production of recombinant nerve growth factors from the NGF/BDNF family. Specifically, the present invention describes a method for producing biologically active recombinant NGF, BDNF, NT3 and NT4.

BACKGROUND OF THE INVENTION

Neurotrophic factors are natural proteins, found in the nervous system or in non-nerve tissues innervated by the nervous system, whose function is to promote the survival and maintain the phenotypic differentiation of nerve and/or glial cells (Varon and Bunge (1978) *Ann. Rev. Neurosc.* 1:327; Thoenen and Edgar (1985) *Science* 229:238). In vivo studies have shown that a variety of endogenous and exogenous neurotrophic factors exhibit a trophic effect on neuronal cells after ischemic, hypoxic, or other disease-induced damage. Examples of specific neurotrophic factors include basic fibroblast growth factor (bFGF), acidic fibroblast growth factor (aFGF), nerve growth factor (NGF), ciliary neurotrophic factor (CNTF), brain derived neurotrophic factor (BDNF), neurotrophin 3 (NT3), neurotrophin 4 (NT4), and the insulin-like growth factors I and II (IGF-I, IGF-II).

Some neurotrophic factors, such as bFGF and CNTF, are thought to have broad trophic effects, promoting survival or providing a maintenance function for many different types of neuronal cells. Other neurotrophic factors have a narrower, more specific trophic effect and promote survival of fewer types of cells. For example, in the peripheral nervous system NGF promotes neuronal survival and axonal extension of certain specific neuronal cells types such as sensory and sympathetic neurons (Ebendal et al. (1984) *Cellular and Molecular Biology of Neuronal Development*, Ch. 15, ed. Black, I.B.). However, in the central nervous system (CNS), NGF also supports the survival of cholinergic neurons in the basal forebrain complex (Whittemore et al. (1987) *Brain Res. Rev.* 12:439–464).

BDNF, a basic protein of molecular weight 12,300, supports some sensory neurons that do not respond to NGF (Barde et al. (1982) *EMBO J.* 1:549–553 and Hofer and Barde (1988) *Nature* 331:261–262). Neurotrophin 3 (NT3) supports survival of dorsal root ganglion neurons and proprioceptive neurons in the trigeminal mesencephalic nucleus. CNTF, a protein of about molecular weight 23,000, supports ciliary ganglion neurons in the parasympathetic nervous system, sympathetic neurons, dorsal root ganglion neurons in the sensory nervous system, and motor neurons in the CNS (Kandel et al. (1991) *Principles of Neural Science*, 3rd Ed., Elsevier Science Publishing Co., Inc., N.Y.).

Some neurotrophic factors constitute a family of neurotrophic factors characterized by about 50% amino acid homology. One such family is the NGF/BDNF family, which includes BDNF, NGF, NT3 and NT4 (Hohn et al. WO 91/03569; U.S. patent application Ser. No. 07/680,681 now abandoned). Both NGF and BDNF are apparently synthesized as larger precursor forms which are then processed, by proteolytic cleavages, to produce the mature neurotrophic factor (Edwards et al. (1986) *Nature* 319:784; Leibrock et al. (1989) *Nature* 319:149). There is a significant similarity in amino acid sequences between mature NGFs and mature BDNF, including the relative position of all six cysteine amino acid residues, which is identical in mature NGFs and BDNF from all species examined (Leibrock et al. (1989) supra.). See FIG. 2, comparing and emphasizing the similarities of human forms of BDNF (SEQ ID NO:3) and NGF (SEQ ID NO:4). This suggests that the three-dimensional structures of the mature proteins, as determined by the location of the disulfide bonds, are similar. The mature NGFs and BDNF proteins also share a basic isoelectric point (pI).

NGF is a neurotrophic factor at least for cholinergic neurons in the basal forebrain (Hefti and Will (1987) *J. Neural Transm. [Suppl] (AUSTRIA)* 24:309). The functional inactivation and degeneration of the basal forebrain cholinergic neurons responsive to NGF in the course of Alzheimer's disease is thought to be the proximate cause of the cognitive and memory deficits associated with that disease (Hefti and Will (1987) supra.). NGF has been shown to prevent the degeneration and restore the function of basal forebrain cholinergic neurons in animal models related to Alzheimer's disease, and on this basis has been proposed as a treatment to prevent the degeneration and restore the function of these neurons in Alzheimer's disease (Williams et al. (1986) *Proc. Natl. Acad. Sci. USA* 83:9231; Hefti (1986) *J. Neuroscience* 6:2155; Kromer (1987) *Science* 235:214; Fischer et al. (1987) *Nature* 329:65).

BDNF is a neurotrophic factor for sensory neurons in the peripheral nervous system (Barde (1989) *Neuron* 2:1525). On this basis, BDNF may prove useful for the treatment of the loss of sensation associated with damage to sensory nerve cells that occurs in various peripheral neuropathies (Schaumberg et al. (1983) in *Disorders of Peripheral Nerves*, F. A. Davis Co., Philadelphia, Pa.).

In order for a particular neurotrophic factor to be potentially useful in treating nerve damage, it must be available in sufficient quantity to be used as a pharmaceutical treatment. Also, since neurotrophic factors are proteins, it is desirable to administer to human patients only the human form of the protein, to avoid an immunological response to a foreign protein. Since neurotrophic factors are typically present in vanishingly small amounts in tissues (e.g., Hofer and Barde (1988) *Nature* 331:261; Lin et al. (1989) *Science* 246:1023) and since human tissues are not readily available for extraction, it would be inconvenient to prepare pharmaceutical quantities of human neurotrophic factors directly from human tissues. As an alternative, it is desirable to use the isolated human gene for neurotrophic factor in a recombinant expression system to produce potentially unlimited amounts of the human protein.

Mature, biologically-active neurotrophic factors can be produced when human or animal neurotrophic factor genes are expressed in eukaryotic cell expression systems (e.g., Edwards et al. (1988) *Molec. Cell. Biol.* 8:2456). In such systems, the full-length neurotrophic factor precursor is first synthesized and then proteolytically processed to produce mature neurotrophic factor which is correctly folded 3-dimensionally and is fully biologically active. However, eukaryotic cell expression systems often produce relatively low yields of protein per gram of cells and are relatively expensive to use in manufacturing.

In contrast, expression systems that use prokaryotic cells, such as bacteria, generally yield relatively large amounts of expressed protein per gram of cells and are relatively inexpensive to use in manufacturing. However, obtaining biologically active bacterially-expressed neurotrophic factor has been a major hurdle in this field. Bacteria are not able to correctly process precursor proteins, such as the precursor protein for NGF, by making appropriate proteolytic cleavages in order to produce the correct smaller mature protein. Therefore, to produce mature neurotrophic factor in bacteria, it is necessary to express only that portion of the DNA sequence encoding the mature protein and not that for the larger precursor form. When this was done in *E. coli*, relatively large amounts of the mature human NGF protein were produced (see, e.g., Iwai et al. (1986) *Chem. Parm. Bull.* 34:4724; Dicou et al. (1989) *J. Neurosci. Res.* 22:13; European Patent Application 121,338). Unfortunately, the bacterially-expressed protein had no apparent biological activity.

Bacterial production of recombinant mammalian proteins often result in biologically inactive proteins forming inclusion bodies. This necessitates separating the inclusion bodies from other cell components, and solubilizing the inclusion bodies to unfold the protein (Spalding (1991) *Biotechnology* 9:229). The likely reason for this lack of biological activity is that the mature protein is unable to assume spontaneously the correct 3-dimensional structure and form the correct intramolecular disulfide bonding pattern required for full biological activity. Processing includes the separation and solubilization of the inclusion bodies, unfolding the protein, then refolding the protein into the correct biologically active tertiary structure. However, during refolding, the protein may reaggregate, reducing the yield of active protein and further complicating the purification process (Spalding (1991) supra).

Protocols for unfolding and refolding NGF have been described (e.g., European Patent Application 336,324; U.S. Pat. Nos. 4,511,503 and 4,620,948). However, these protocols have serious deficiencies. Many protocols use exposure of NGF to high pH to break incorrectly formed disulfide bonds followed by exposure to lower pH to allow formation of correct intramolecular disulfide bonds. The exposure of NGF to high pH is known to result in extensive modification of the protein, including elimination of amine side chains in glutamine and asparagine (of which there are 7 in mature human NGF), and extensive chemical alteration of asparagine-glycine, asparagine-serine, and asparagine-threonine adjacent pairs (of which there are 2 in mature human NGF). In addition to these chemical modifications, the refolding procedure appeared to restore only approximately one-tenth of the biological activity of NGF. Although numerous protocols for refolding and renaturing proteins that do not involve harsh conditions exist, no such procedure has been applied successfully to NGF. For a general review of refolding procedures, see Kohno (1990) *Methods Enzymol.* 185:187.

Various methods have been used to improve recovery of biologically active proteins produced in a bacterial expression system. One method for cleaving incorrectly formed disulfide bonds is the use of S-sulfonated proteins obtained by sulfitolysis (U.S. Pat. No. 4,421,685; Gonzalez and Damodaran (1990) *J. Agric. Food Chem.* 38:149; European Patent Application 361,830). The addition of sulfite to a protein initially cleaves the disulfide bonds exposed to the solution, resulting in the formation of one $S-SO_3^-$ derivative and one free SH group for each disulfide bond cleaved. In the presence of an oxidizing agent, the free SH groups are oxidized back to disulfide, which is again cleaved by the sulfite present in the system. The reaction cycle repeats itself until all the disulfide bonds and the sulfhydryl groups in the protein are converted to $cys-SO_3^-$. Generally, this allows most proteins to be fully solubilized (European Patent Application 361,830).

Another method to improve the recovery of biologically active protein from bacterial expression systems includes the use of polyethylene glycol (PEG) in the refolding mixture. It has been proposed that the addition of PEG prevents protein aggregation resulting from the association of hydrophobic intermediates in the refolding pathway. Cleland et al. (1990) *Biotechnology* 8:1274 and (1992) *J. Biol. Chem.* 267:13327, reported improved recovery of biologically active bovine carbonic anhydrase B (CAB) with the addition of PEG during the refolding process. The concentration of PEG required to achieve an increase in the recovery of active protein was twice the total protein concentration, and required PEG with molecular weights of 1000–8000 (Cleland et al. (1992) supra).

A bacterial expression system for producing NGF is disclosed in Canadian Patent No. 1,220,736 and U.S. Pat. No. 5,169,762. However, no procedures for refolding the expressed protein are presented. A procedure for producing large quantities of biologically active recombinant NGF suitable for pharmaceutical use is described in U.S. patent application Ser. No. 08/087,912 filed Jul. 6, 1993 now abandoned by Collins et al., entitled: *Production of Biologically Active, Recombinant Members of the NGF/BDNF Family of Neurotrophic Proteins*. The protein is exposed to a denaturant, such as guanidine hydrochloride or urea, and sufficient reducing agent, such as β-mercaptoethanol, dithiothreitol, or cysteine, to denature the protein, disrupt noncovalent interactions, and reduce disulfide bonds. The free thiols present in the reduced protein are then oxidized, and the protein allowed to form the correct disulfide bonds. The refolding mixture preferably contained up to 25% PEG 200 or 300.

While the procedure described in U.S. patent application Ser. No. 08/087,912 now abandoned achieves improved yields of biologically active NGF, the need remains for more efficient means for refolding NGF. The bacterial production of recombinant proteins results in biologically inactive proteins found as inclusion bodies within the bacterial cell. There is a need for improved processing methods for separating the inclusion bodies from other cell components and solubilizing the inclusion bodies to unfold the protein. Further, there is a need for improved methods for breaking incorrectly formed disulfide bonds and refolding the protein into the correct tertiary structure required for maximum yield of fully active protein while decreasing chemical modification of the protein.

The present disclosure presents an extended and improved method for producing bacterially-expressed biologically active members of the NGF/BDNF family of neurotrophic factors, including the first use of the process of sulfitolysis to solubilize and chemically modify a neurotrophic factor.

BRIEF SUMMARY OF THE INVENTION

The present invention discloses a process for the production of mature proteins from the NGF/BDNF family in a fully biologically active form suitable for therapeutic use comprising:

a) expressing a gene coding for the neurotrophic factor in a bacterial expression system wherein said neurotrophic factor protein is produced;

b) solubilizing said neurotrophic factor in urea;

c) sulfonylating said neurotrophic factor;

d) isolating and purifying the sulfonylated neurotrophic factor;

e) allowing the sulfonylated neurotrophic factor to refold to give the biologically active neurotrophic factor; and f) purifying the biologically active neurotrophic factor.

Sulfonylated neurotrophic factor is purified by anion exchange chromatography and refolded in the presence of 20% polyethylene glycol 300 (PEG 300). Refolded neurotrophic factor is purified by cation exchange chromatography.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE FIGURES

FIG. 1 compares the nucleic acid sequence of human BDNF (SEQ ID NO:1) and NGF (SEQ ID NO:2). Gaps, indicated by dashes, correspond to the location of gaps used to align the amino acid sequences.

FIG. 2 compares the amino acid sequences of human BDNF (SEQ ID NO:3) and NGF (SEQ ID NO:4). The inferred sequences of the mature proteins are in bold. Gaps, indicated by dashes were placed in the sequences to increase alignment. The six cysteins found in BDNF and NGF are found in the same locations and are bracketed.

FIG. 3 shows the synthetic NGF sequence (SEQ ID NO:5) inserted into *E. coli* and expressed as the mature NGF protein.

FIG. 4 shows the sequences of Mut1 (SEQ ID NO:6), Mut2 (SEQ ID NO:7), and Mut3 (SEQ ID NO:8) oligonucleotides used to correct the NGF sequence.

FIG. 5 shows the Syn NGF 5P oligonucleotide sequence used for making enhanced expression of NGF (SEQ ID NO:9).

FIG. 6 shows the TP NGF (SEQ ID NO:10) and REP NGF (SEQ ID NO:11) oligonucleotide sequences used for making the TP (TNF binding protein) NGF REP construct.

FIG. 7 shows the TP Δ53 nucleic acid sequence (SEQ ID NO:12).

FIG. 8 shows the oligonucleotide sequence used for making the TP NGF(2start-)REP construct (SEQ ID NO:13).

DESCRIPTION OF THE PREFERRED EMBODIMENTS

Figure 9A:
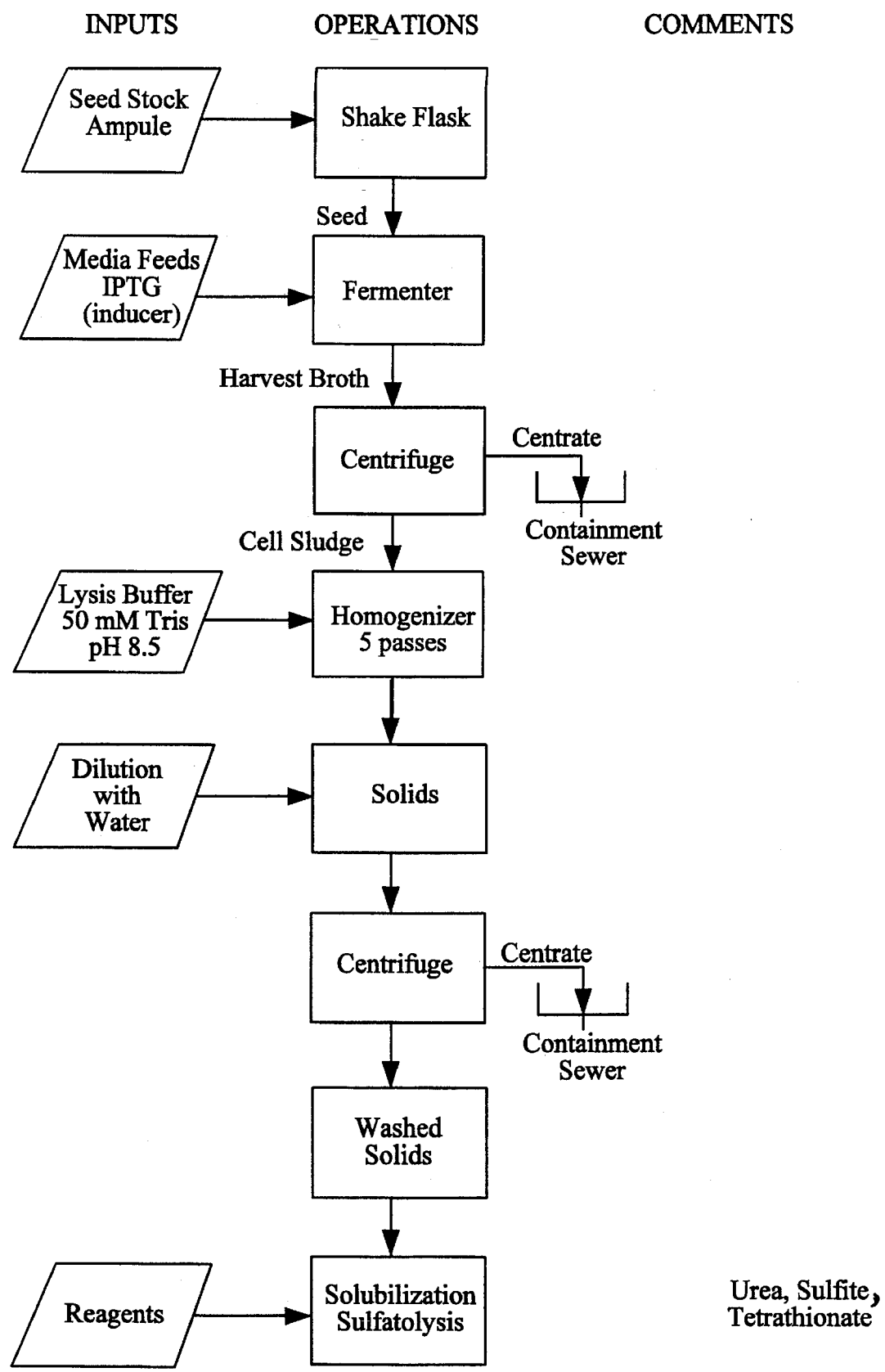
FIG. 9 shows a process flow diagram for the process of this invention.

Reference will now be made in detail to the presently preferred embodiments of the invention which, together with the following examples, serve to explain the principles of the invention.

The present invention is an extended and improved method for producing bacterially-expressed biologically active neurotrophic factors from the NGF/BDNF family from that disclosed in the earlier application U.S. patent application Ser. No. 08/087,912 now abandoned, specifically incorporated herein by reference.

The production method of this invention for obtaining the fully biologically active mature human recombinant neurotrophic factor from the NGF/BDNF family is comprised of:

a) expressing neurotrophic factor in a bacterial expression system;

b) solubilizing and sulfonylating neurotrophic factor;

c) refolding sulfonylated neurotrophic factor such that the correct tertiary structure necessary for full biological activity is obtained; and d) purifying the fully biologically active neurotrophic factor.

The present invention relates to an improved method for the efficient production of recombinant neurotrophic factors in the nerve growth factor (NGF) and brain derived neurotrophic factor (BDNF) family. The invention herein described is a process of producing a "family" of neurotrophic growth factors in a pure and biologically active form suitable for therapeutic use. NGF is a member of a family of structurally related neurotrophic proteins which are likely to differ in their physiological role in the organism, each member affecting a different set of responsive neurons. Known members of the NGF family include NGF, BDNF, NT3 and NT4. Each of these members have significant homology and identical number of cysteine residues and location. The present invention encompasses recombinant proteins that code for proteins which are not identical to human NGF or BDNF but are clearly related to NGF or BDNF with respect to possible defining characteristics of the family. Such characteristics may include one or more of the following: neurotrophic activity in an appropriate bioassay; significant homology in amino acid sequence including both amino acid identities and conservative substitutions; conserved location of cysteine residues in the amino acid sequence; hydrophobic signal sequences for secretion of the protein; signal sequences for proteolytic processing to a mature form; and/or basic isoelectric point of the processed protein.

As used in the disclosure, the term "biological activity" when applied to NGF means proteins having the biological activity of NGF, that is for example, the ability to promote the survival of chick embryo sympathetic chain and dorsal root ganglia neurons in the bioassay described in Example 3. For other members of the NGF/BDNF family, "biological activity" means neurotrophic activity in the appropriate bioassay.

This invention encompasses the production of neurotrophic proteins of any origin which are biologically equivalent to the neurotrophic proteins of the NGF/BDNF family. In the preferred embodiment, this invention encompasses mature human neurotrophic proteins. Throughout this specification, any reference to a neurotrophic protein should be construed to refer to the proteins identified and described herein as members of the NGF/BDNF family of neurotrophic proteins.

By "biologically equivalent" used throughout the specification and claims, we mean compositions of the present invention which are capable of promoting the survival and maintaining the phenotypic differentiation of nerve or glial cells, but not necessarily to the same degree as the native neurotrophic proteins described herein. Biologically equivalent compositions include fragments of proteins exhibiting NGF/BDNF family-like neurotrophic activity. Further encompassed by the present invention are the amino acid sequences shown in FIG. 2 and those substantially homologous, with 1, 2, 3, or 4 amino acid residue changes or deletions which do not substantially alter neurotrophic activity. This invention further includes chemically modified sequences substantially homologous to those shown in FIG. 2, for example, by addition of polyethylene glycol.

By "substantially homologous" as used throughout the ensuing specification and claims, it is meant a degree of homology to the native neurotrophic proteins in excess of that displayed by any previously reported neurotrophic proteins. Preferably, the degree of homology is in excess of 70%, most preferably in excess of 80%, and even more preferably in excess of 90%, 95%, or 99%. A particularly preferred group of neurotrophic proteins are in excess of 95% homologous with the native proteins. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., specifically incorporated herein by reference. Also included as substantially homologous are those neurotrophic proteins which may be isolated by virtue of cross-reactivity with antibodies to the described protein or whose genes may be isolated through hybridization with the gene or with segments of the described protein.

Members of the NGF/BDNF family of neurotrophic factors are naturally produced as larger precursor forms which are then processed by proteolytic cleavages to produce the "mature" protein (Edwards et al. (1986) supra; Leibrock et al. (1989) supra.). Because bacterial expression systems are unable to correctly process the precursor form of the protein, only that portion of the DNA sequence coding for the mature protein is expressed in a bacterial expression system.

In one embodiment of the present invention, a synthetic NGF DNA sequence is constructed which is optimized for production in an *E. coli* expression system. The synthetic NGF gene may be constructed with a DNA sequence coding for human or animal NGF. The synthetic NGF gene is cloned into a vector capable of being transferred into and replicated in the host cell, such vector containing operational elements needed to express the DNA sequence. The construction of a preferred synthetic NGF gene and cloning into a vector suitable for transfer into an *E. coli* expression system is described in Example 1. This invention encompasses the use of a synthetic neurotropic factor gene from the NGF/BDNF family, as well as a synthetic gene with substantial homology to a gene from the NGF/BDNF family.

A natural or synthetic DNA sequence may be used to direct production of NGF. The synthetic NGF gene described in Example 1, shown in FIG. 3 (SEQ ID NO:5), was specifically designed to direct expression of the mature human NGF protein in a bacterial expression system. Codons for certain amino acids were optimized for expression in *E. coli* as well as to create restriction sites to facilitate subsequent cloning steps. The general expression method comprised:

1. preparation of a DNA sequence capable of directing *E. coli* to produce mature human NGF;

2. cloning the DNA sequence into a vector capable of being transferred into and replicated in *E. coli*, such vector containing operational elements needed to express the NGF sequence;

3. transferring the vector containing the synthetic DNA sequence and operational elements into *E. coli* host cells; and 4. culturing the *E. coli* host cells under conditions for amplification of the vector and expression of NGF.

The host cells are cultured under conditions appropriate for the expression of NGF. These conditions are generally specific for the host cell, and are readily determined by one of ordinary skill in the art in light of the published literature regarding the growth conditions for such cells and the teachings contained herein. For example, *Bergey's Manual of Determinative Bacteriology*, 8th Ed., Williams & Wilkins Company, Baltimore, Md., which is specifically incorporated herein by reference, contains information on culturing bacteria. In the preferred embodiment of the present invention, NGF is produced in an *E. coli* expression system. The present invention encompasses the use of this production method to produce any neurotrophic factor from the NGF/BDNF family.

A method for the production of recombinant members of the human NGF/BDNF family of neurotrophic proteins in biologically active forms is described in U.S. patent application Ser. No. 08/087,912 now abandoned (Collins et al.). Collins et al. disclose a method for refolding and renaturing recombinant human mature members of the NGF/BDNF family of neurotrophic proteins. Any intramolecular or intermolecular disulfide bonds and/or any noncovalent interactions which have occurred involving mature neurotrophic protein produced in a microorganism are first disrupted. In order to do this, the protein is exposed to sufficient denaturant such as guanidine hydrochloride or urea, and sufficient reducing agent such as β-mercaptoethanol, dithiothreitol, or cysteine, to denature the protein, disrupt noncovalent interactions, and reduce disulfide bonds. After the mature neurotrophic protein is denatured and reduced, the free thiols present in the reduced protein are oxidized by addition of a large excess of disulfide-containing reagent, such as glutathione or cystine. This reaction produces mixed disulfide bonds in which each cysteine residue in the mature neurotrophic protein forms a disulfide bond with the monomeric form of the oxidizing agent. The denaturant and oxidizing agent are then diluted to a definite concentration and a thiol-containing reagent such as cysteine is added to catalyze disulfide interchange. This creates an environment in which the denaturant concentration is sufficiently reduced to allow the neurotrophic protein to assume various 3-dimensional configurations and in which the oxidation/reduction potential is adjusted to allow the formation and breaking of disulfide bonds. It is assumed that a significant proportion of the neurotrophic protein will form the correct intramolecular disulfide bonding pattern, and therefore, the correct 3-dimensional structure and attain biological activity. Collins et al. further disclose the use of up to 25% polyethylene glycol (PEG) 200, 300, or 1000 added to the final refolding mixture. In the presence of PEG, a greater than 30% increase is obtained in the amount of properly-refolded biologically-active NGF. The Collins et al. method represents an improvement over the harsh conditions of the prior art methods, achieving protein with up to 50% of biological activity.

The production method of the present invention represents an extension and improvement over the method described by Collins et al. in several ways. The process of sulfitolysis is used to solubilize the insoluble protein produced in E. coli. Sulfitolysis imparts several important advantages to the NGF purification process over all prior art methods. Sodium sulfite is a strong reductant and functions at least as well as 2-mercaptoethanol or dithiothreitol in solubilizing NGF from the washed solids. NGF fully reduced in the presence of urea does not resolve as a clear peak on chromatographic resins. In contrast, sulfonylated-NGF shows a marked improvement in resolution on ion-exchange resins. Further, sulfitolysis imparts a negative charge to the protein for each cysteine which has been modified. Each monomer of NGF contains six cysteine residues, and thus the fully sulfonylated monomeric form contains an additional six negative charges. This represents several advantages: 1) the increase in the total charge on each monomer increases its hydrophilicity and solubility; 2) the additional negative charges lower the effective isoelectric point of the protein. This allows the use of anion exchange chromatography at a lower pH than is possible with the fully reduced form of the protein. Additionally, this allows for the purification of a urea-solubilized form of the protein with an apparent pI of about 7.5, followed by purification of the soluble refolded form of the protein with a theoretical pI of about 10.4. The ability to purify two forms of the same protein which exhibit different apparent isoelectric points provided the basis for the high level of separation of NGF away from contaminating E. coli proteins.

Example 2 describes the refolding and purification process of the present invention after expression of NGF in the E. coli expression system. The E. coli host cells are lysed, and the fraction containing NGF isolated as the "NGF washed solids suspension".

NGF is solubilized and sulfonylated in the presence of urea and sulfite.

Sulfonylated NGF may be captured and purified by anion exchange chromatography by several different schemes. In one embodiment, described in detail in Example 2, sulfonylated NGF is diluted with Buffer A (8 M urea, 20 mM Tris-HCl, pH 9.0), applied to an anion exchange column, and eluted with Buffer B (8 M urea, 36 mM MES, pH 6.0). In another embodiment, sulfonylated NGF was eluted from the column with a linear gradient from Buffer A to Buffer B. In a preferred embodiment of the invention, sulfonylated NGF was diafiltered against Buffer A in an ultrafiltration cartridge, applied to an anion exchange column, and eluted with a linear gradient from Buffer A to Buffer B. In another preferred embodiment, sulfonylated NGF was concentrated and diafiltered in an ultrafiltration membrane in a stirred cell, applied to an anion exchange column, and eluted as above.

Purified sulfonylated NGF may be refolded by several methods, as described in Example 2. Urea and PEG were added to a carboy and the solution cooled. NGF was added, the pH adjusted, and solid cysteine added. The carboy was then stored at 10° C. for 4 days.

Properly refolded NGF was captured by cation exchange chromatography. Refolded NGF was recovered as a single peak of protein which contained several altered charged species of NGF. Incorrectly charged forms of NGF were purified away from the main NGF peak and concentrated.

Although the following examples describe each step of the process of the present invention for the production of biologically-active NGF, the present invention encompasses the production of biologically active neurotrophic factors from the NGF/BDNF family, including BDNF, NGF, NT3, and NT4, as well as neurotrophic factors having substantial homology and similar biological activity. The degree of homology existing between members of the NGF/BDNF family of neurotrophic factors, including amino acid sequence and location of disulfide bonds, suggests that these proteins have similar three-dimensional structures. Further, the problems associated with incorrect formation of disulfide bonds and the need for improved methods for refolding and renaturing the bacterially produced protein are similar for all members of the NGF/BDNF family of neurotrophic factors.

Example 1. Construction of a Synthetic NGF Gene and Expression in E. coli.

A synthetic NGF gene was designed to optimize the codons for expression in E. coli as well as create unique restriction sites to facilitate subsequent cloning steps.

The NGF gene was assembled in two pieces: 1) Section A—a 218 base pair (bp) BamHI-SalI piece of DNA consisting of 3 pairs of complementary oligonucleotides synthesized on an Applied Biosystems 380A DNA synthesizer; 2) Section B—a 168 bp SalI-KpnI piece of DNA consisting of 2 pairs of complementary synthetic oligonucleotides (FIG. 3)(SEQ ID NO:5).

A. Assembly of the Sections. Each oligonucleotide was phosphorylated using T4 polynucleotide kinase. The phosphorylated oligonucleotides were then annealed to their complements by heating to 80° C. and slow cooling to 35° C. The pairs of oligonucleotides (3 for Section A and 2 for Section B) were ligated and subsequently digested with BamHI-SalI (Section A) or SalI-KpnI (Section B) to minimize multiple insertions. The resulting fragments were isolated on 5% polyacrylamide gel and eluted. Each fragment was ligated into a pUC18 fragment digested with the appropriate enzymes (BamHI and SalI for Section A; SalI and KpnI for Section B). JM109 was transformed and isolates were grown in Luria broth with ampicillin added at a concentration of 100 µg/ml. Plasmid DNA was prepared and confirmed to have the appropriately sized fragment by restriction digest analysis.

B. Assembly of the Entire Synthetic NGF Gene. A BamHI-SalI 218 bp fragment was isolated from Section A pUC18 and a 168 bp SalI-KpnI fragment was isolated from Section B pUC18 as done above using a 5% polyacrylamide gel. These fragments were ligated into BamHI-KpnI cut pUC18 (IPTG and XGal were used to colorimetrically determine colonies with inserts with white colonies having inserts). A white colony was chosen and plasmid DNA prepared. When a BamHI-KpnI digest was done, a 387 bp fragment was released and isolated from a 1% agarose gel. The 387 bp fragment was ligated into a BamHI-KpnI, approximately 7 kilobase (Kb) vector fragment, REP pT3XI-2, obtained from a digest of plasmid TP NGF (2start-)REP pT2XI-2. REP is a repetitive extragenic palindrome sequence reported to stabilize messenger RNA by preventing 3'–5' exonucleolytic activity Merino et al. (1987) Gene 58:305). A transformant was grown in Luria broth and tetracycline at a concentration of 10 µg/ml. Plasmid DNA was prepared and digested with BamHI-KpnI. A 387 bp fragment was observed but in order to ensure that the fragment was the synthetic gene, a second digest was done with BamHI-EcoRV (the EcoRV site is eliminated from the coding region of the synthetic gene). When the construct was sequenced, three areas appeared to have the wrong sequence and were corrected through in vitro mutagenesis using a Mutagene kit purchased from Biorad. The areas of concern were between nucleotides 83–91 (Mut1)(FIG. 4, SEQ ID NO:6), nucleotide 191 (Mut2)(FIG. 4, SEQ ID NO:7), and a deletion of 2 C's at nucleotides 258 and 259

(Mut3)(FIG. 4, SEQ ID NO:8). The synthetic NGF gene was ligated into BamHI-KpnI cut mp18 as a BamHI-KpnI fragment to use as a template for the mutagenesis. The mutagenesis was done in a 2 step process, first using oligonucleotides Mut1 and Mut2 for a double mutagenesis. Two isolates with the correct sequence were chosen by hybridization to $^{32}$P-labelled Mut1 and Mut2 oligonucleotides (called Mut1,2A and Mut1,2B). These were then mutagenized with Mut3 oligonucleotide in a second step and one isolate from each plate was chosen by hybridization to a $^{32}$P-labelled Mut3 probe (Syn NGF MutA and Syn NGF MutB). Both isolates had the correct sequence. Replicative form (RF—double stranded DNA) was prepared and digested with BamHI-KpnI and a 387 bp fragment isolated from a 1% agarose gel. The Syn NGF MutA fragment was ligated into a 7 Kb BamHI-KpnI vector fragment, REP pT3XI-2, isolated from TP NGF REP pT3XI-2. MCB00005 was transformed, one isolate grown in Luria broth plus tetracycline at a concentration of 10 µg/ml, and plasmid DNA was prepared. A diagnostic BamHI-KpnI digest was done to confirm the presence of the insert.

C. Enhanced Synthetic NGF. As a means of boosting expression of the synthetic gene, the region between the initiating methionine and BamHI site was altered through in vitro mutagenesis to resemble that of a highly expressed T7 bacteriophage protein, gene 10, using the oligonucleotide, Syn NGF 5P (FIG. 5)(SEQ ID NO:9). Syn NGF MutA mp18 was used as the template. Four plaques were chosen by hybridizing to a $^{32}$P-labelled Syn NGF 5P oligonucleotide. RF DNA was made and digested with BamHI-KpnI. All had the appropriately sized fragment and the sequence of each was also correct. The BamHI-KpnI 387 bp fragment was isolated from a 1% agarose gel and ligated into a BamHI-KpnI, approximately 7 Kb vector fragment, REP pT3XI-2 (isolated from BamHI-KpnI digested Syn NGF A REP pT3XI-2 described above). MCB00005 was transformed. Colonies were screened with $^{32}$P-labelled Syn NGF 5P oligonucleotide and 2 colonies that hybridized to the probe were grown in Luria broth plus tetracycline at a concentration of 10 µg/ml. Both isolates had the correct sequence.

D. Construction of TP NGF REP pT3XI-2 and TP NGF (2start-) REP pT3XI-2.

(1) TP NGF REP PT3XI-2. DH5α carrying a BamHI-HindIII fragment of the British Biotechnology NGF gene (British Biotechnology, Limited, Oxford, England) was digested with BamHI-HindIII, a 380 base pair fragment was isolated, and ligated into BamHI-HindIII digested mp18. The DNA was in vitro mutagenized in a 2-step process. The first step involved insertion of a BamHI site immediately 3' to the HindIII site at the 5' end of the gene and also insertion of a Shine-Delgarno (S/D) sequence with "optimal" spacing for efficient expression between the S/D and initiating Met codon (see TP NGF oligonucleotide, FIG. 6)(SEQ ID NO:10). A plaque was chosen after hybridizing to the $^{32}$P-labelled TP NGF oligonucleotide (FIG. 6)(SEQ ID NO:10). A second round of mutagenesis was done using the oligonucleotide REP NGF (FIG. 6) (SEQ ID NO:11). A plaque was chosen through hybridization with $^{32}$P labelled REP NGF oligonucleotide. RF DNA was prepared, an approximately 470 Kb BamHI-HindIII fragment isolated, and ligated into an approximately 7 Kb BamHI-HindIII vector fragment isolated from Bam TP Δ53 pT3XI-2 (FIG. 7)(SEQ ID NO:12). Strain MCB00005 was transformed and an isolate chosen, sequenced, and found to have the correct sequence.

(2) TP NGF (2start-) pT3XI-2. In order to eliminate a putative second initiation region within the NGF gene, in vitro mutagenesis was done using the oligonucleotide, 2start- (FIG. 8)(SEQ ID NO:13), and TP NGF REP mp18 as the template. An isolate that hybridized to $^{32}$P-labelled 2start- oligonucleotide was sequenced and found to have the correct sequence. RF DNA was prepared, a BamHI-HindIII approximately 470 bp fragment was isolated from a 1% agarose gel, and ligated into an approximately 7 Kb BamHI-HindIII fragment, pT3XI-2 (isolated from Bam TP Δ53 pT3XI-2, see FIG. 7 (SEQ ID NO:12)). MCB00005 was transformed, and the correct isolate determined through restriction digest analysis.

Example 2. Isolation of Biologically Active NGF.

A. Cell Lysis. The human recombinant NGF gene construct of Example 1 was expressed in *E. coli* cells grown in chemically defined medium at 33° C. A fresh or frozen slurry of cells was diluted with 50 mM Tris-HCl, 10 mM EDTA, pH 8.5, to a final solids concentration of about 20% (weight/volume). Cells were lysed using 4 passes through a Gaulin or Rannie homogenizer at a pressure of >8000 PSI. The lysate was passed through a cooling coil to maintain the temperature at less than 15° C.

B. Harvest and wash of cell solids containing NFG. Cell solids were captured using a Westphalia centrifuge. After the capture the percent of solids was determined. Sufficient cold wash/dilution buffer (20 mM Tris-HCl, pH 7.5) was added to lower the percent solids to 5 percent. After gentle mixing the lysate went for a second pass through the centrifuge. The final "NGF washed cell suspension" was assayed for percent solids. Approximately 80 g of washed solids were recovered per Kg of starting cells. The "NGF washed solids suspension" was either used immediately or was frozen at -20° C. for subsequent use.

C. Solubilization and chemical modification of NGF. The NGF present in the washed solids was solubilized by the use of 8 M urea and a sulfitolysis mixture. This resulted in solubilized, denatured, chemically-modified NGF in which the cysteine residues are present as a cys-SO$_3^{31}$ mixed disulfide.

Sufficient solid urea and water were added to the "NGF washed solids suspension" to achieve a final concentration of 8 M urea in a final volume equal to twice the volume of washed solids suspension used. After dissolution of the urea, the following final concentrations of reagents were added for the step of sulfitolysis: 10 mM Tris buffer, 100 mM sodium sulfite, 10 mM sodium tetrathionate. The mixture was brought to a final pH of about 7.5 with HCl and stirred at room temperature for at least about 2 hours.

D. Capture and purification of sulfonylated NGF. Sulfonylated NGF was captured and purified from the sulfitolysis mixture by anion exchange chromatography. Several loading and eluting schemes were utilized.

In one embodiment of the invention, the sulfitolysis mixture was diluted 10-fold in Buffer A (8 M urea, 20 mM Tris-HCl, pH 9.0), and adjusted to a final pH of 9.0 with NaOH. This solution was applied to a column of Pharmacia Q-Sepharose big bead resin equilibrated with Buffer A. A volume representing 25 grams of NGF washed solids was loaded per liter of resin. The column was washed with 3 column volumes of Buffer A. Sulfonylated NGF was eluted by lowering the pH using Buffer B (8 M urea, 36 mMMES, pH 6.0). In another embodiment of the invention, sulfonylated NGF was eluted with a linear gradient from Buffer A to Buffer B in about 10 column volumes.

In the preferred embodiment of the invention, an alternate loading procedure utilized diafiltration of the sulfitolysis mixture using either an Amicon S1Y10 or S10Y10 spiral wrap ultrafiltration cartridge. The mixture was diafiltered with about 4 volumes of Buffer A. This diafiltered sulfitolysis mixture was adjusted to pH 9.0 and applied directly to a column of Q-Sepharose big bead resin. A volume representing 125 grams of NGF washed solids was loaded per liter of resin. The column was washed and the sulfonylated NGF was eluted as described above.

The protein eluted from the columns by any of the above described methods was primarily sulfonylated NGF. The peak of eluted protein was pooled and the protein concentration was determined by absorbance at 280 nm using an extinction coefficient of 1.44. Column yields of up to about 5 mg of protein per gram of NGF washed solids were typical.

E. Refolding NGF. Q-Sepharose-purified, sulfonylated NGF may be refolded by several methods. In the preferred embodiment, sulfonylated NGF was refolded at a final protein concentration of 0.1 mg/ml. The required final refold volume was calculated based on the amount of protein to be refolded. Filtered, deionized 8M urea, polyethylene glycol 300 (PEG 300), dibasic potassium phosphate and water were combined in a carboy such that final concentrations of 5M urea, 20% PEG 300 and 100 mM dibasic potassium phosphate were attained in the final refold volume. The solution was cooled to about 10° C. Sulfonylated NGF was gently added to a final concentration of 0.1 mg/ml. The pH of this mixture was brought to about 8.7 with 5 M HCl. Stirring was halted and L-cysteine was added to a final concentration of 3 mM. The gas phase was sparged for about 5 minutes with a vigorous stream of argon, and the carboy was sealed. The solution was stirred until the L-cysteine was dissolved, and the carboy was stored at about 10° C. for about 4 days.

Refolding efficiency was studied with NGF protein concentrations ranging between 0.02 and 0.2 mg/ml. Refolding efficiency improved with decreasing protein concentration, however the required volumes and the cost of the refold reagents precluded optimization based solely on yield. Urea concentrations between 4.5 and 5.5 M proved optimal for refold. Yields fell off sharply below about 4 M urea, while concentrations above 5.5 M proved impractical.

Optimal refold was achieved using about 20% PEG 300. PEG 200 functioned nearly as well as PEG 300. Lower levels of PEG 300, or of PEG 200, or replacement of the PEG with ethylene glycol led to much lower refold efficiencies.

Refolding efficiencies were examined with phosphate concentrations between zero and 0.5 M. NGF refolding exhibited a broad optimum between 100 and 200 mM phosphate. A comparison of monobasic sodium phosphate, dibasic sodium phosphate, monobasic potassium phosphate, and dibasic potassium phosphate showed only minor differences in NGF refold efficiencies. Dibasic potassium phosphate was preferred for its starting pH in solution and for its increased solubility over the comparable sodium salt.

NGF refolded optimally at about 10° C., although temperatures between 4° C. and 15° C. worked nearly as well. Refold fell sharply above 15° C., with negligible refold occurring at room temperature. Increases in the pH of the refold solution led to large changes in the rate of refolding. For example, at pH 8.3 refolding took 8–9 days to near completion, while at pH 8.7 refolding was near complete after 4 days. Higher pH was avoided due to the urea present in the refold solution, the length of the refold, and the increased susceptibility of proteins to carbamylation with increasing pH.

L-cysteine or cysteamine were used with equal effectiveness to initiate NGF refolding. Cysteamine hydrochloride was slightly less effective. A final concentration of about 3 mM L-cysteine was optimal. L-cysteine concentrations below 2 mM or above 5 mM lead to a substantial decrease in refolding.

F. Capture of refolded NGF. Properly refolded NGF present in the refold solution was captured using cation exchange chromatography. The column size was chosen based upon the ability of the column to handle the required flow rate and backpressure encountered when loading a large volume of a viscous refold mixture, rather than on the protein loading capacity of the resin. A typical 70-liter refold was captured using a 750 ml resin bed volume.

In the preferred embodiment for the capture of refolded NGF, the carboy was opened after storage at approximately 10° C. for 4 days, and the refold solution was brought to pH 5.0 with either 5 M HCl or with acetic acid. This solution was applied to a column of Pharmacia SP-Sepharose big bead resin which had been equilibrated in 20 mM sodium acetate, pH 5.0. After loading, the column was washed with 4 column volumes of 20 mM sodium acetate, pH 5.0. Soluble, refolded NGF was eluted from the column using 20 mM sodium acetate, 750 mM NaCl, pH 5.0. The flow rate was 0.5 column volumes per minute (c.v./min) during equilibration, loading and washing, and was lowered to 0.25 c.v./min during elution.

A single peak of protein was recovered which was comprised of properly refolded NGF. Although this material appeared near homogeneous by sizing, SDS-PAGE, and standard reverse phase HPLC, it was subsequently shown to contain several altered charged species of NGF by isoelectric focusing and cation exchange HPLC. The principal species separated by cation exchange HPLC were identified as truncated or carbamylated variants of NGF using electrospray mass spectroscopy. It thus became necessary to include an additional column in the purification process to remove these NGF variants.

G. Removal of NGF variants by ion exchange chromatography. In the preferred embodiment of this invention, the pool of protein eluted from the S-Sepharose big bead column was diluted two-fold using 20 mM sodium acetate, pH 5.0, and loaded onto a column of Pharmacia SP-Sepharose high performance resin equilibrated in 20 mM sodium acetate, pH 5.0. The column was loaded to about 5 mg NGF/ml resin. The column was first washed with about 2 column volumes of 20 mM sodium acetate, pH 5.0, then with about 2 column volumes of 20 mM Tris-HCl, 75 mM NaCl, pH 7.5, and eluted with a 12 column volumes linear gradient from 125 to 300 mM NaCl in 20 mM Tris-HCl, pH 7.5. In an alternate embodiment of the invention, the column was washed with about 3 column volumes of 20 mM sodium phosphate buffer, 150 mM NaCl, pH 7.0. Protein was eluted from the column using a 10 column volumes pH gradient from 20 mM sodium phosphate, 150 mM NaCl, pH 7.0, to 20 mM Tris-HCl, 150 mM NaCl, pH 8.0. Both of the above elution schemes led to resolution of incorrect charge forms of NGF away from the main peak of NGF.

Additional embodiments of the invention include the use of other cation exchange resins, such as Pharmacia Mono-S, or elution of the protein with different buffer systems, and/or at a different pH. These included 20 mM glycylglycine, pH 8.5, 50–200 mM NaCl gradient; 20 mM borate, pH 8.0–8.5, 50–300 mM NaCl gradient; 20 mM Tris-HCl, pH 7.0–8.5, 50–400 mM NaCl gradient; and 20 mM sodium phosphate, pH 7.0, 100–500 mM NaCl gradient. NGF was also eluted from the above column using 20 mM sodium acetate buffer, pH 5.0, 450–800 mM NaCl gradient, and with 20 mM sodium citrate, pH 5.0, 400–700 mM NaCl gradient.

H. Concentration/Diafiltration. Fractions containing purified NGF from the SP-Sepharose HP column were pooled, concentrated and exchanged into a final bulk formulation containing citrate and NaCl at pH about 5.2 using an Amicon YM10 membrane in a stirred cell. This step was done at room temperature, with the protein concentration maintained below 5 mg/ml.

I. Precipitation of NGF. Purified NGF exhibited a tendency to precipitate under certain conditions. Factors which led to increased precipitation included increased protein concentration, increased NaCl concentration, increased pH, and decreased temperature. Thus, in the preferred embodiment of this invention, the protein concentration of NGF solutions are kept below 5 mg/ml, and the solutions are not cooled below about 10° C. except to freeze the purified, formulated bulk.

Example 3. Determination of Biological Activity.

Biological activity of purified NGF was determined by testing its ability to promote the survival of chick embryo sympathetic chain neurons in vitro.

Cultures of chick embryo sympathetic chain and dorsal root ganglia were prepared as previously described (Collins and Lile (1989) Brain Research 502:99). Briefly, sympathetic or dorsal root ganglia were removed from fertile, pathogen-free chicken eggs that had been incubated 8–11 days at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%. After this treatment, ganglia were transferred to a solution consisting of Dulbecco's high glucose Modified Eagle Medium without bicarbonate containing 10% fetal calf serum and 10 mM HEPES, pH 7.2 and mechanically dissociated by trituration approximately 10 times through a glass Pasteur pipet whose opening had been fire polished and constricted to a diameter such that it took 2 seconds to fill the pipet. The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50 µl per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water, and air dried.

10 µl of a serial dilution of the sample to be assayed for neurotrophic activity was added to each well and the dishes were incubated for 20 hours at 37° C. in a humidified atmosphere containing 7.5% $CO_2$. After 18 hours, 15 µl per well of a 1.5 mg/ml solution of the tetrazolium dye MTT in Dulbecco's high glucose modified Eagle Medium without bicarbonate containing 10 mM HEPES, pH 7.2 was added and the cultures placed back in the 37° C. incubator for 4 hours. Then 75 µl of a solution of 6.7 ml of 12 M HCl per liter of isopropanol was added and the contents of each well triturated 30 times to break open the cells and suspend the dye. The absorbance at 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The concentration of trophic activity in trophic units (TU) per ml was defined as the dilution that gave 50% of maximal survival of nerve cells. For example, if the sample gave 50% maximal survival when diluted 1:100,000 the titer was defined as 100,000 TU/ml. Specific activity was determined by dividing the number of trophic units per ml by the concentration of protein per ml in the undiluted sample.

Figure 9B:
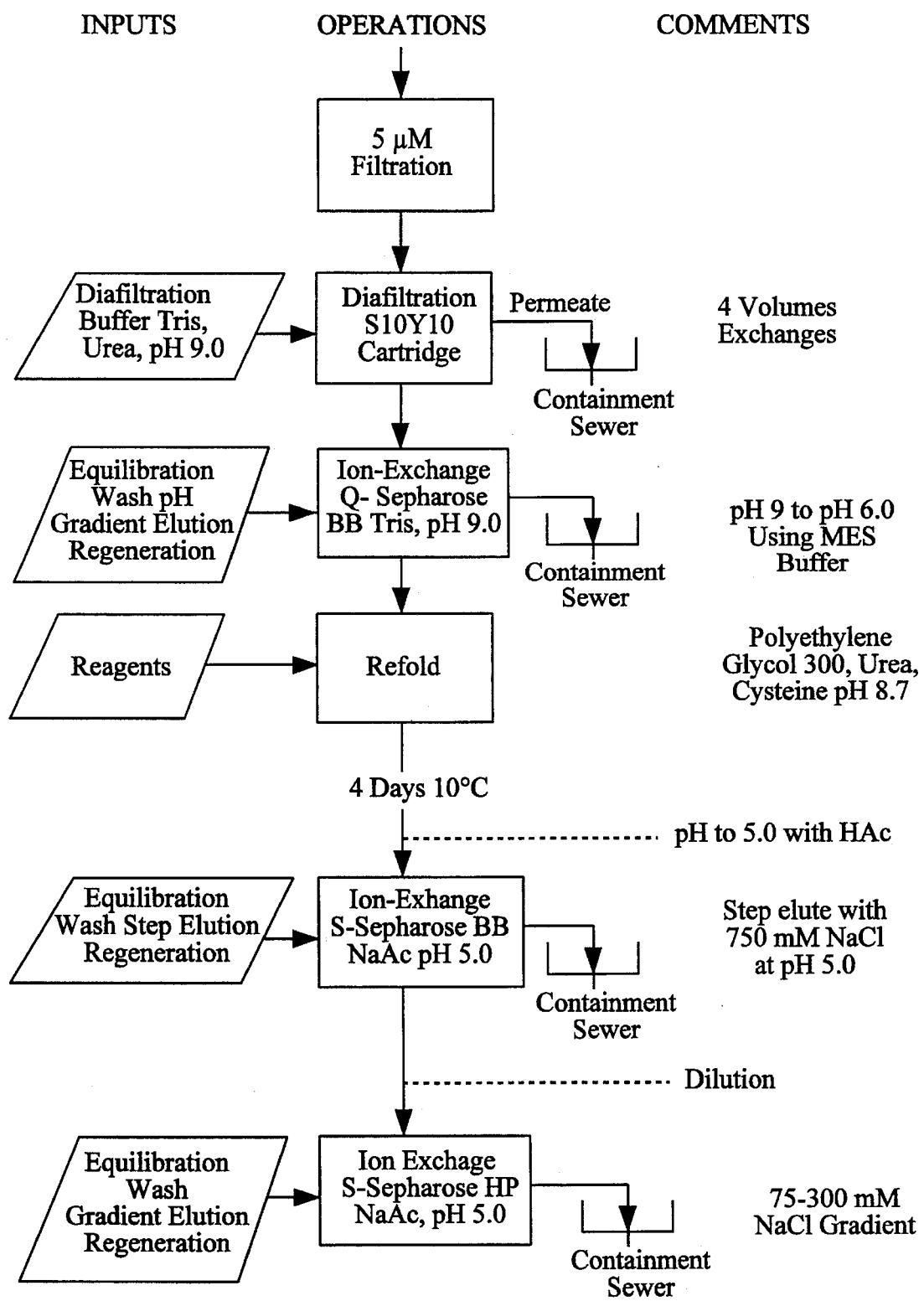
Figure 9C:
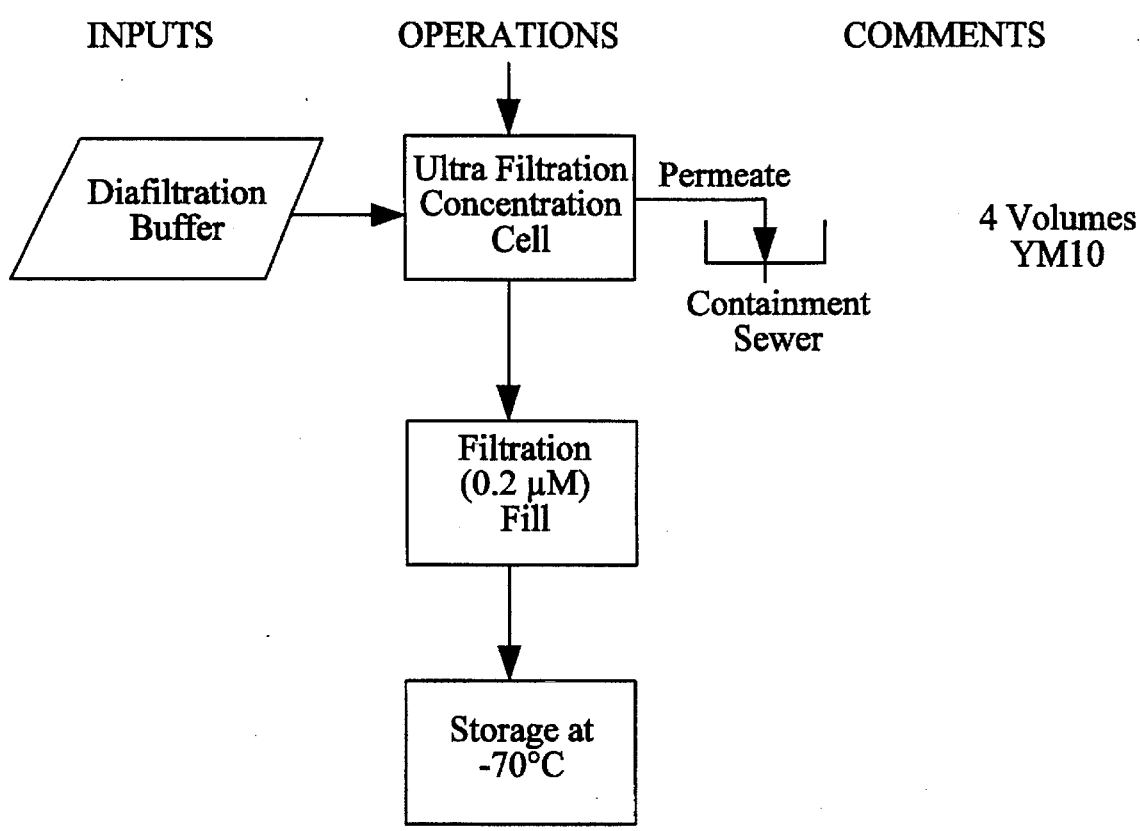

FIG. 9 sets forth the process of this invention in a flow diagram.

---

We claim:

1. A process for the production of biologically active recombinant neurotrophic factor wherein said neurotrophic factor is selected from the group consisting of NGF, BDNF, NT3, and NT4, comprising:
   a) expressing a gene coding for the neurotrophic factor in a bacterial expression system wherein said neurotrophic factor protein is produced;
   b) solubilizing said neurotrophic factor;
   c) sulfonylating said solubilized neurotrophic factor;
   d) isolating and purifying the sulfonylated neurotrophic factor by anion exchange chromatography;
   e) allowing the sulfonylated neurotrophic factor to refold to give the biologically active neurotrophic factor; and
   f) purifying the biologically active neurotrophic factor by cation exchange chromatography.

2. The process of claim 1 wherein said neurotrophic factor gene is comprised of DNA coding for human NGF.

3. The process of claim 1 wherein said neurotrophic factor gene is comprised of DNA coding for animal NGF.

4. The process of claim 1 wherein the neurotrophic factor gene is comprised of the sequence of FIG. 1 (SEQ ID NO:1).

5. The process of claim 1 wherein the neurotrophic gene is comprised of DNA coding for human BDNF.

6. The process of claim 1 wherein the neurotrophic gene is comprised of the sequence of FIG. 1 (SEQ ID NO:2).

7. The process of claim 1 wherein said neurotrophic factor is solubilized in step (b) with 8M urea.

8. The process of claim 1 wherein said neurotrophic factor refolds in step (e) in the presence of polyethylene glycol (PEG) with a molecular weight of between 200–300.

9. The process of claim 8 wherein said refolding step (e) further comprises the presence of PEG in the concentration of between 15–20% (weight/volume), and urea in the concentration range of 4.5–5.5 M, wherein the final protein concentration of neurotrophic factor is about 0.1 mg/ml, and the refolding step (e) takes place at a temperature of about 10° C.

10. The process of any of claims 1, 7, or 8 wherein refolding step (e) is initiated with the addition of one of L-cysteine or cysteamine.

11. The process of claim 1 wherein sulfonylated neurotrophic factor is isolated and purified in step (d) by utilizing concentration and diafiltration.

12. A process for the production of biologically active recombinant neurotrophic factor, wherein said neurotrophic factor is selected from the group consisting of NGF, BDNF, NT3, and NT4, comprising:
   a) constructing a synthetic neurotrophic factor DNA gene for directing an *E. coli* expression system to produce a neurotrophic factor;
   b) expressing said neurotrophic factor in the *E. coli* expression system;
   c) solubilizing and sulfonylating said neurotrophic factor;
   d) purifying said solubilized and sulfonylated neurotrophic factor using anion exchange chromatography;
   e) refolding said purified and sulfonylated neurotrophic factor such that the correct tertiary structure necessary for full biological activity is obtained; and
   f) purifying the fully biologically active neurotrophic factor by cation exchange chromatography.

13. The process of claim 12 wherein said neurotrophic factor gene is comprised of DNA coding for human NGF.

14. The process of claim 12 wherein said neurotrophic factor gene is comprised of DNA coding for animal NGF.

15. The process of claim 12 wherein the neurotrophic factor gene is comprised of the sequence of FIG. 1 (SEQ ID NO:1).

16. The process of claim 12 wherein the neurotrophic gene is comprised of DNA coding for human BDNF.

17. The process of claim 12 wherein the neurotrophic gene is comprised of the sequence of FIG. 1 (SEQ ID NO:2).

18. The process of claim 12 wherein said neurotrophic factor is solubilized in step (c) with 8M urea.

19. The process of claim 12 wherein said neurotrophic factor refolds in step (e) in the presence of polyethylene glycol (PEG) with a molecular weight of between 200–300.

20. The process of claim 19 wherein said refolding step (e) further comprises the presence of PEG in the concentration of about 20% (weight/volume), urea in the concentration range of 4.5–5.5 M, wherein the final protein concentration of neurotrophic factor is about 0.1 mg/ml, and the refolding step (e) takes place at a temperature of about 10° C.

21. The process of any of claims 12, 18, or 19 wherein refolding step (e) is initiated with the addition of one of L-cysteine or cysteamine.

22. The process of claim 12 wherein sulfonylated neurotrophic factor is isolated and purified in step (d) by utilizing concentration and diafiltration.

* * * * *

UNITED STATES PATENT AND TRADEMARK OFFICE
CERTIFICATE OF CORRECTION

PATENT NO.   : 5,606,031
DATED        : February 25, 1997
INVENTOR(S)  : Jack Lile, Tadahiko Kohno, Duane Bonam and Mary S. Rosendahl It is certified that error appears in the above-identified patent and that said Letters Patent is hereby corrected as shown below:

Column 5, line 41, correct "cysteins" to read --cysteines--.

Column 6, line 51, after "survival", insert --and proliferation--.

line 52, delete "neurons".

Column 12, line 41, correct "cys-$SO_3^{31}$" to read --cys-$SO^3$--.

Signed and Sealed this

Twenty-third Day of March, 1999

Attest:

Q. TODD DICKINSON

Attesting Officer    Acting Commissioner of Patents and Trademarks

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 742 nucleotides
        ( B ) TYPE: nucleic acid
        ( C ) STRANDEDNESS: single
        ( D ) TOPOLOGY: linear ( i x ) FEATURE:
        ( A ) NAME/KEY: nucleic acid sequence for human BDNF ( x i ) SEQUENCE DESCRIPTION: SEQ ID NO:1:

```
ATGCATCCTT  TTCCTTACTA  TGGTTATTTC  ATACTTTGGT  TGCATGAAGG         50

CTGCCCCCAT  GAAAGAAGCA  AACATCCGAG  GACAAGGTGG  CTTGGCCTAC        100
```

| | | | | | |
|---|---|---|---|---|---|
| CCAGGTGTGC | GGACCCATGG | GACTCTGGAG | AGCGTGAATG | GGCCCAAGGC | 150 |
| AGGTTCAAGA | GGCTTGACAT | CATTGGCTGA | CACTTTCGAA | CACGTGATAG | 200 |
| AAGAGCTGTT | GGATGAGGAC | CAGAAAGTTC | GGCCCAATGA | AGAAAACAAT | 250 |
| AAGGACGCAG | ACTTGTACAC | GTCCAGGGTG | ATGCTCAGTA | GTCAAGTGCC | 300 |
| TTTGGAGCCT | CCTCTTCTCT | TTCTGCTGGA | GGAATACAAA | AATTACCTAG | 350 |
| ATGCTGCAAA | CATGTCCATG | AGGGTCCGGC | GCCACTCTGA | CCCTGCCCGC | 400 |
| CGAGGGGAGC | TGAGCGTGTG | TGACAGTATT | AGTGAGTGGG | TAACGGCGGC | 450 |
| AGACAAAAAG | ACTGCAGTGG | ACATGTCGGG | CGGGACGGTC | ACAGTCCTTG | 500 |
| AAAAGGTCCC | TGTATCAAAA | GGCCAACTGA | AGCAATACTT | CTACGAGACC | 550 |
| AAGTGCAATC | CCATGGGTTA | CACAAAAGAA | GGCTGCAGGG | GCATAGACAA | 600 |
| AAGGCATTGG | AACTCCCAGT | GCCGAACTAC | CCAGTCGTAC | GTGCGGGCCC | 650 |
| TTACCATGGA | TAGCAGAAAG | AGAATTGGCT | GGCGATTCAT | AAGGATAGAC | 700 |
| ACTTCTTGTG | TATGTACATT | GACCATTAAA | AGGGGAAGAT | AG | 742 |

( 2 ) INFORMATION FOR SEQ ID NO:2:

( i ) SEQUENCE CHARACTERISTICS:
        ( A ) LENGTH: 725 nucleotides
        ( B ) TYPE: nucleic acid
        ( C ) STRANDEDNESS: single
        ( D ) TOPOLOGY: linear ( i x ) FEATURE:
        ( A ) NAME/KEY: nucleic acid sequence for human NGF ( x i ) SEQUENCE DESCRIPTION: SEQ ID NO:2:

| | | | | | |
|---|---|---|---|---|---|
| ATGTCCATGT | TGTTCTACAC | TCTGATCACA | GCTTTTCTGA | TCGGCATACA | 50 |
| GGCGGAACCA | CACTCAGAGA | GCAATGTCCC | TGCAGGACAC | ACCATCCCCC | 100 |
| AAGTCCACTG | GACTAAACTT | CAGCATTCCC | TTGACACTGC | CCTTCGCAGA | 150 |
| GCCCGCAGCG | CCCCGGCAGC | GGCGATAGCT | GCACGCGTGG | CGGGGCAGAC | 200 |
| CCGCAACATT | ACTGTGGACC | CCAGGCTGTT | TAAAAAGCGG | CGACTCCGTT | 250 |
| CACCCCGTGT | GCTGTTTAGC | ACCCAGCCTC | CCCGTGAAGC | TGCAGACACT | 300 |
| CAGGATCTGG | ACTTCGAGGT | CGGTGGTGCT | GCCCCCTTCA | ACAGACTCAC | 350 |
| AGGAGCAAGC | GGTCATCATC | CCATCCCATC | TTCCACAGGG | GCGAATTCTC | 400 |
| GGTGTGTGAC | AGTGTCAGCG | TGTGGGTTGG | GGATAAGACC | ACCGCCACAG | 450 |
| ACATCAAGGG | CAAGGAGGTG | ATGGTGTTGG | GAGAGGTGAA | CATTAACAAC | 500 |
| AGTGTATTCA | AACAGTACTT | TTTTGAGACC | AAGTGCCGGG | ACCCAAATCC | 550 |
| CGTTGACAGC | GGGTGCCGGG | GCATTGACTC | AAAGCACTGG | AACTCATATT | 600 |
| GTACCACGAC | TCACACCTTT | GTCAAGGCGC | TGACCATGGA | TGGCAAGCAG | 650 |
| GCTGCCTGGC | GGTTTATCCG | GATAGATACG | GCCTGTGTGT | GTGTGCTCAG | 700 |
| CAGGAAGGCT | GTGAGAAGAG | CCTGA | | | 725 |

( 2 ) INFORMATION FOR SEQ ID NO:3:

( i ) SEQUENCE CHARACTERISTICS:
        ( A ) LENGTH: 247 amino acids
        ( B ) TYPE: amino acid
        ( C ) TOPOLOGY: linear ( i x ) FEATURE:

(A) NAME/KEY: inferred amino acid sequence of human BDNF (xi) SEQUENCE DESCRIPTION: SEQ ID NO:3:

```
Met Thr Ile Leu Phe Leu Thr Met Val Ile Ser Tyr Phe Gly Cys Met
        -125             -120                 -115
Lys Ala Ala Pro Met Lys Glu Ala Asn Ile Arg Gly Gln Gly Gly Leu
        -110             -105                 -100
Ala Tyr Pro Gly Val Arg Thr His Gly Thr Leu Glu Ser Val Asn Gly
    -95              -90                  -85
Pro Lys Ala Gly Ser Arg Gly Leu Thr Ser Leu Ala Asp Thr Phe Glu
-80              -75                  -70                      -65
His Val Ile Glu Glu Leu Leu Asp Glu Asp Gln Lys Val Arg Pro Asn
                -60               -55                      -50
Glu Glu Asn Asn Lys Asp Ala Asp Leu Tyr Thr Ser Arg Val Met Leu
            -45              -40                     -35
Ser Ser Gln Val Pro Leu Glu Pro Pro Leu Leu Phe Leu Leu Glu Glu
        -30              -25                  -20
Tyr Lys Asn Tyr Leu Asp Ala Ala Asn Met Ser Met Arg Val Arg Arg
    -15              -10                  -5
His Ser Asp Pro Ala Arg Arg Gly Glu Leu Ser Val Cys Asp Ser Ile
 1               5                   10                   15
Ser Glu Trp Val Thr Ala Ala Asp Lys Lys Thr Ala Val Asp Met Ser
            20                  25                  30
Gly Gly Thr Val Thr Val Leu Glu Lys Val Pro Val Ser Lys Gly Gln
            35                  40                  45
Leu Lys Gln Tyr Phe Tyr Glu Thr Lys Cys Asn Pro Met Gly Tyr Thr
        50                  55                  60
Lys Glu Gly Cys Arg Gly Ile Asp Lys Arg His Trp Asn Ser Gln Cys
65                  70                  75                   80
Arg Thr Thr Gln Ser Tyr Val Arg Ala Leu Thr Met Asp Ser Arg Lys
                85                  90                  95
Arg Ile Gly Trp Arg Phe Ile Arg Ile Asp Thr Ser Cys Val Cys Thr
            100                 105                 110
Leu Thr Ile Lys Arg Gly Arg
            115
```

(2) INFORMATION FOR SEQ ID NO:4:

(i) SEQUENCE CHARACTERISTICS:
    (A) LENGTH: 241 amino acids
    (B) TYPE: amino acid
    (C) TOPOLOGY: linear (ix) FEATURE:
    (A) NAME/KEY: inferred amino acid sequence of human NGF (xi) SEQUENCE DESCRIPTION: SEQ ID NO:4:

```
Met Ser Met Leu Phe Tyr Thr Leu Ile Thr Ala Phe Leu Ile Gly Ile
    -120             -115                 -110
Gln Ala Glu Pro His Ser Glu Ser Asn Val Pro Ala Gly His Thr Ile
-105             -100                  -95                     -90
Pro Gln Val His Trp Thr Lys Leu Gln His Ser Leu Asp Thr Ala Leu
            -85                  -80                      -75
Arg Arg Ala Arg Ser Ala Pro Ala Ala Ala Ile Ala Ala Arg Val Ala
        -70                  -65                     -60
Gly Gln Thr Arg Asn Ile Thr Val Asp Pro Arg Leu Phe Lys Lys Arg
        -55                  -50                     -45
```

| Arg | Leu | Arg | Ser | Pro | Arg | Val | Leu | Phe | Ser | Thr | Gln | Pro | Pro | Arg | Glu |
|---|---|---|---|---|---|---|---|---|---|---|---|---|---|---|---|
| -40 | | | | | | -35 | | | | | -30 | | | | |

| Ala | Ala | Asp | Thr | Gln | Asp | Leu | Asp | Phe | Glu | Val | Gly | Gly | Ala | Ala | Pro |
|---|---|---|---|---|---|---|---|---|---|---|---|---|---|---|---|
| -25 | | | | | -20 | | | | -15 | | | | | | -10 |

| Phe | Asn | Arg | Thr | His | Arg | Ser | Lys | Arg | Ser | Ser | His | Pro | Ile | Phe |
|---|---|---|---|---|---|---|---|---|---|---|---|---|---|---|
| | | | | -5 | | | | | 1 | | | | 5 | |

| His | Arg | Gly | Glu | Phe | Ser | Val | Cys | Asp | Ser | Val | Ser | Val | Trp | Val | Gly |
|---|---|---|---|---|---|---|---|---|---|---|---|---|---|---|---|
| | | 10 | | | | | 15 | | | | | 20 | | | |

| Asp | Lys | Thr | Thr | Ala | Thr | Asp | Ile | Lys | Gly | Lys | Glu | Val | Met | Val | Leu |
|---|---|---|---|---|---|---|---|---|---|---|---|---|---|---|---|
| | 25 | | | | | 30 | | | | | 35 | | | | |

| Gly | Glu | Val | Asn | Ile | Asn | Asn | Ser | Val | Phe | Lys | Gln | Tyr | Phe | Phe | Glu |
|---|---|---|---|---|---|---|---|---|---|---|---|---|---|---|---|
| 40 | | | | | 45 | | | | | 50 | | | | | 55 |

| Thr | Lys | Cys | Arg | Asp | Pro | Asn | Pro | Val | Asp | Ser | Gly | Cys | Arg | Gly | Ile |
|---|---|---|---|---|---|---|---|---|---|---|---|---|---|---|---|
| | | | | 60 | | | | | 65 | | | | | 70 | |

| Asp | Ser | Lys | His | Trp | Asn | Ser | Tyr | Cys | Thr | Thr | Thr | His | Thr | Phe | Val |
|---|---|---|---|---|---|---|---|---|---|---|---|---|---|---|---|
| | | | 75 | | | | | 80 | | | | | 85 | | |

| Lys | Ala | Leu | Thr | Met | Asp | Gly | Lys | Gln | Ala | Ala | Trp | Arg | Phe | Ile | Arg |
|---|---|---|---|---|---|---|---|---|---|---|---|---|---|---|---|
| | | | 90 | | | | | 95 | | | | 100 | | | |

| Ile | Asp | Thr | Ala | Cys | Val | Cys | Val | Leu | Ser | Arg | Lys | Ala | Val | Arg | Arg |
|---|---|---|---|---|---|---|---|---|---|---|---|---|---|---|---|
| | 105 | | | | | 110 | | | | | 115 | | | | |

Ala
120

( 2 ) INFORMATION FOR SEQ ID NO:5:

( i ) SEQUENCE CHARACTERISTICS:
( A ) LENGTH: 389 nucleotides
( B ) TYPE: nucleic acid
( C ) STRANDEDNESS: double
( D ) TOPOLOGY: linear ( x i ) SEQUENCE DESCRIPTION: SEQ ID NO:5:

```
GGATCCAATA AGGAGGAAAA AAA ATG TCT AGC AGC CAC CCG ATC TTT CAT CGT          53
                          Met Ser Ser Ser His Pro Ile Phe His Arg
                           1               5                  10

GGC GAA TTC TCT GTA TGC GAT TCC GTT AGC GTT TGG GTT GGC GAC AAA           101
Gly Glu Phe Ser Val Cys Asp Ser Val Ser Val Trp Val Gly Asp Lys
             15                  20                  25

ACC ACT GCT ACT GAC ATC AAA GGT AAA GAA GTA ATG GTT CTG GGC GAA           149
Thr Thr Ala Thr Asp Ile Lys Gly Lys Glu Val Met Val Leu Gly Glu
         30                  35                  40

GTT AAC ATC AAC AAT TCT GTT TTT AAA CAG TAC TTC TTC GAA ACC AAA           197
Val Asn Ile Asn Asn Ser Val Phe Lys Gln Tyr Phe Phe Glu Thr Lys
         45                  50                  55

TGC CGC GAC CCG AAC CCG GTC GAC TCC GGC TGC CGT GGT ATC GAC TCT           245
Cys Arg Asp Pro Asn Pro Val Asp Ser Gly Cys Arg Gly Ile Asp Ser
         60                  65                  70

AAA CAC TGG AAC TCC TAC TGC ACC ACT ACT CAC ACC TTC GTT AAA GCT           293
Lys His Trp Asn Ser Tyr Cys Thr Thr Thr His Thr Phe Val Lys Ala
 75                  80                  85                  90

CTG ACC ATG GAC GGC AAA CAG GCT GCA TGG CGT TTT ATT CGT ATT GAC           341
Leu Thr Met Asp Gly Lys Gln Ala Ala Trp Arg Phe Ile Arg Ile Asp
             95                 100                 105

ACC GCA TGT GTT TGC GTA CTG AGC CGC AAA GCT GTT CGT TAAGGTACC             389
Thr Ala Cys Val Cys Val Leu Ser Arg Lys Ala Val Arg
            110                 115
```

( 2 ) INFORMATION FOR SEQ ID NO:6:

( i ) SEQUENCE CHARACTERISTICS:

(A) LENGTH: 32 nucleotides
(B) TYPE: nucleic acid
(C) STRANDEDNESS: single
(D) TOPOLOGY: linear (xi) SEQUENCE DESCRIPTION: SEQ ID NO:6:

CGATTCCGTT AGCGTTTGGG TTGGCGACAA AA    32

(2) INFORMATION FOR SEQ ID NO:7:

(i) SEQUENCE CHARACTERISTICS:
(A) LENGTH: 21 nucleotides
(B) TYPE: nucleic acid
(C) STRANDEDNESS: single
(D) TOPOLOGY: linear (xi) SEQUENCE DESCRIPTION: SEQ ID NO:7:

CTTCTTGGAA ACCAAATCCC G    21

(2) INFORMATION FOR SEQ ID NO:8:

(i) SEQUENCE CHARACTERISTICS:
(A) LENGTH: 22 nucleotides
(B) TYPE: nucleic acid
(C) STRANDEDNESS: single
(D) TOPOLOGY: linear (xi) SEQUENCE DESCRIPTION: SEQ ID NO:8:

CACTGGAACT CCTACTGCAC CA    22

(2) INFORMATION FOR SEQ ID NO:9:

(i) SEQUENCE CHARACTERISTICS:
(A) LENGTH: 35 nucleotides
(B) TYPE: nucleic acid
(C) STRANDEDNESS: single
(D) TOPOLOGY: linear (xi) SEQUENCE DESCRIPTION: SEQ ID NO:9:

GGATCCAAGA AGGAGATATA CATATGTCTA GCAGC    35

(2) INFORMATION FOR SEQ ID NO:10:

(i) SEQUENCE CHARACTERISTICS:
(A) LENGTH: 43 nucleotides
(B) TYPE: nucleic acid
(C) STRANDEDNESS: single
(D) TOPOLOGY: linear (xi) SEQUENCE DESCRIPTION: SEQ ID NO:10:

TGCCAAGCTT GGATCCAAGA AGGAGATATA CATATGTCAT CAT    43

(2) INFORMATION FOR SEQ ID NO:11:

(i) SEQUENCE CHARACTERISTICS:
(A) LENGTH: 119 nucleotides
(B) TYPE: nucleic acid
(C) STRANDEDNESS: single
(D) TOPOLOGY: linear (xi) SEQUENCE DESCRIPTION: SEQ ID NO:11:

GGCTGTGAGA TAAGGTACCG ACATTGCCTG ATGGCGCTGT GCGTGTCAGG    50

CCTACGGGGA GCATCGTAGG CCGGGCAAGG CACAGCCGCC ATCCGGCGTG    100

CCCAAGCTTG GATCCCCGG    119

(2) INFORMATION FOR SEQ ID NO:12:

( i ) SEQUENCE CHARACTERISTICS:
  ( A ) LENGTH: 691 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:12:

| | | | | | | |
|---|---|---|---|---|---|---|
| GCTGTTGACA | ATTAATCATC | GGCTCGTATA | ATGTGTGGAA | TTGTGAGCGG | | 50 |
| ATAACAATTT | CACACAGGAA | ACAGAATTCC | ACAACGGTTT | CCCTCTAGAA | | 100 |
| ATAATTTTGT | TTGGATCCAA | GAAGGAGATA | TACAT ATG TTG CCC | | | 144 |
| | | | Met Leu Pro | | | |
| | | | 1 | | | |

```
GCC  CAG  GTG  GCA  TTT  ACA  CCC  TAC  GCT  CCG  GAA  CCG  GGT          183
Ala  Gln  Val  Ala  Phe  Thr  Pro  Tyr  Ala  Pro  Glu  Pro  Gly
      5                        10                     15

TCT  ACC  TGC  CGG  CTC  AGA  GAA  TAC  TAT  GAC  CAG  ACA  GCT          222
Ser  Thr  Cys  Arg  Leu  Arg  Glu  Tyr  Tyr  Asp  Gln  Thr  Ala
                20                         25

CAG  ATG  TGC  TGC  AGC  AAG  TGC  TCG  CCG  GGC  CAA  CAT  GCA          261
Gln  Met  Cys  Cys  Ser  Lys  Cys  Ser  Pro  Gly  Gln  His  Ala
 30                        35                         40

AAA  GTC  TTC  TGT  ACC  AAG  ACC  TCG  GAC  ACC  GTG  TGT  GAC          300
Lys  Val  Phe  Cys  Thr  Lys  Thr  Ser  Asp  Thr  Val  Cys  Asp
           45                        50                          55

TCC  TGT  GAG  GAC  AGC  ACA  TAC  ACC  CAG  CTC  TGG  AAC  TGG          339
Ser  Cys  Glu  Asp  Ser  Thr  Tyr  Thr  Gln  Leu  Trp  Asn  Trp
                     60                         65

GTT  CCC  GAG  TGC  TTG  AGC  TGT  GGC  TCC  CGC  TGT  AGC  TCT          378
Val  Pro  Glu  Cys  Leu  Ser  Cys  Gly  Ser  Arg  Cys  Ser  Ser
      70                        75                     80

GAC  CAG  GTG  GAA  ACT  CAA  GCC  TGC  ACT  CGG  GAA  CAG  AAC          417
Asp  Gln  Val  Glu  Thr  Gln  Ala  Cys  Thr  Arg  Glu  Gln  Asn
                85                         90

CGC  ATC  TGC  ACC  TGC  AGG  CCC  GGC  TGG  TAC  TGC  GCG  CTG          456
Arg  Ile  Cys  Thr  Cys  Arg  Pro  Gly  Trp  Tyr  Cys  Ala  Leu
 95                       100                        105

AGC  AAG  CAG  GAG  GGG  TGC  CGG  CTG  TGC  GCG  CCG  CTG  CGC          495
Ser  Lys  Gln  Glu  Gly  Cys  Arg  Leu  Cys  Ala  Pro  Leu  Arg
           110                       115                        120

AAG  TGC  CGC  CCG  GGC  TTC  GGC  GTG  GCC  AGA  CCA  GGA  ACT          534
Lys  Cys  Arg  Pro  Gly  Phe  Gly  Val  Ala  Arg  Pro  Gly  Thr
                     125                       130

GAA  ACA  TCA  GAC  GTG  GTG  TGC  AAG  CCC  TGT  GCC  CCG  GGG          573
Glu  Thr  Ser  Asp  Val  Val  Cys  Lys  Pro  Cys  Ala  Pro  Gly
 135                       140                       145

ACG  TTC  TCC  AAC  ACG  ACT  TCA  TCC  ACG  GAT  ATT  TGC  AGG          612
Thr  Phe  Ser  Asn  Thr  Thr  Ser  Ser  Thr  Asp  Ile  Cys  Arg
           150                       155

CCC  CAC  CAG  ATC  TGT  AAC  GTG  GTG  GCC  ATC  CCT  GGG  AAT          651
Pro  His  Gln  Ile  Cys  Asn  Val  Val  Ala  Ile  Pro  Gly  Asn
 160                       165                       170

GCA  AGC  AGG  GAT  GCA  GTC  TGC  ACG  TCC  ACG  TCC  TAA  GCTT         691
Ala  Ser  Arg  Asp  Ala  Val  Cys  Thr  Ser  Thr  Ser
           175                       180
```

( 2 ) INFORMATION FOR SEQ ID NO:13:

( i ) SEQUENCE CHARACTERISTICS:
    ( A ) LENGTH: 33 nucleotides
    ( B ) TYPE: nucleic acid
    ( C ) STRANDEDNESS: single (D) TOPOLOGY: linear (xi) SEQUENCE DESCRIPTION: SEQ ID NO:13:

```
TCAAGGGCAA AGAAGTGATG GTATTGGGAG AGG                    33
```